United States Patent [19]

Wenderoth et al.

[11] Patent Number: 4,997,973

[45] Date of Patent: Mar. 5, 1991

[54] ORTHO-SUBSTITUTED BENZYL CARBOXYLATES AND FUNGICIDES CONTAINING THESE COMPOUNDS

[75] Inventors: Bernd Wenderoth, Lampertheim; Siegbert Brand, Weinheim; Franz Schuetz, Ludwigshafen; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 322,974

[22] Filed: Mar. 14, 1989

[30] Foreign Application Priority Data

Apr. 12, 1988 [DE] Fed. Rep. of Germany ....... 3812082

[51] Int. Cl.$^5$ ............................................ C07C 69/176
[52] U.S. Cl. ........................................ 560/55; 558/12; 560/54; 560/53
[58] Field of Search ...................... 560/55, 53; 170/24; 558/12; 514/531, 532

[56] References Cited

U.S. PATENT DOCUMENTS

| | | | |
|---|---|---|---|
| 4,709,078 | 11/1987 | Schirmer et al. | 560/60 |
| 4,723,034 | 2/1988 | Schirmer et al. | 560/60 |
| 4,782,177 | 11/1988 | Schirmer et al. | 560/60 |
| 4,822,908 | 4/1989 | Karbach et al. | 514/522 |
| 4,829,085 | 5/1989 | Wenderoth et al. | 514/522 |

FOREIGN PATENT DOCUMENTS 226917 12/1986 European Pat. Off. .
2202844 10/1985 United Kingdom .

Primary Examiner—Paul J. Killos
Attorney, Agent, or Firm—Oblon, Spivak, McClelland, Maier & Neustadt

[57] ABSTRACT

Benzyl carboxylates of the formula

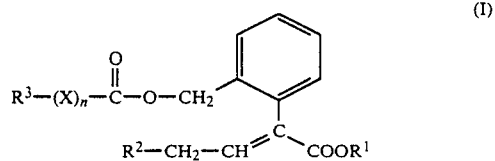

where
$R^1$ is alkyl,
$R^2$ is hydrogen, alkyl or alkoxy,
$R^3$ is hydrogen, halogen, cyano, aryl or aryloxy, the aromatic ring being unsubstituted or substituted, or $R^3$ is heteroaryl, adamantyl, fluorenyl or cycloalkyl or cycloalkenyl, the radicals being unsubstituted or substituted,
X is saturated or unsaturated, substituted or unsubstituted alkylene, and
n is 0 or 1, and fungicides containing these compounds.

21 Claims, No Drawings

ORTHO-SUBSTITUTED BENZYL CARBOXYLATES AND FUNGICIDES CONTAINING THESE COMPOUNDS

The present invention relates to novel ortho-substituted benzyl carboxylates, their preparation and their use as fungicides.

It is known that N-tridecyl-2,6-dimethylmorpholine or its salts, for example the acetate, can be used as fungicides (DE 1 164 152 and 1 173 722). However, their action is unsatisfactory in some cases. It is also known that methyl α-[(2-phenoxymethylene)-phenyl]- or α-[(2-alkoxymethylene)-phenyl]-β-methoxyacrylate can be used as fungicides (DE-35 45 319.2 and DE-36 20 860.4). However, their action is unsatisfactory.

We have found that novel ortho-substituted benzyl carboxylates of the formula I

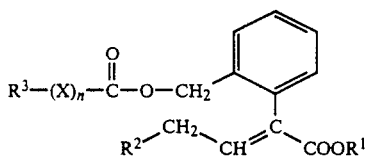

(I)

where $R^1$ is $C_1$–$C_5$-alkyl, $R^2$ is hydrogen, $C_1$–$C_4$-alkyl or $C_1$–$C_4$-alkoxy, $R^3$ is hydrogen, halogen, cyano, aryl or aryloxy, the aromatic ring being unsubstituted or substituted by one or more of the following radicals: $C_1$–$C_6$-alkyl, $C_2$–$C_4$-alkenyl, $C_1$- or $C_2$-haloalkyl, $C_1$–$C_6$-alkoxy, $C_1$–$C_4$-alkoxy-$C_1$–$C_4$-alkyl, aryl, aryl-$C_1$- or $C_2$-alkyl, aryloxy, aryloxy-$C_1$–$C_4$-alkyl, aryloxy-$C_1$–$C_4$-alkoxy, haloaryloxy-$C_1$–$C_4$- alkoxy, halogen, halo-$C_1$–$C_4$-alkoxy, $C_1$–$C_4$-alkylthio, thiocyanato, cyano and nitro, or $R^3$ is hetaryl adamantyl fluorenyl or $C_3$–$C_7$-cycloalkyl or $C_5$- or $C_6$-cycloalkenyl, the radicals being unsubstituted or substituted by $C_1$–$C_4$-alkyl (methyl or ethyl), halogen (chlorine or bromine), $C_1$- or $C_2$-haloalkyl (trifluoromethyl, tetrabromoethyl or dichlorodibromoethyl), $C_3$- or $C_4$-alkenyl (methylvinyl or dimethylvinyl), $C_2$–$C_4$-haloalkenyl (dichlorovinyl, dichlorobutadienyl, difluorovinyl or trifluoromethylvinyl), methoxycarbonyl-$C_3$- or $C_4$-alkenyl (methylmethoxycarbonylvinyl), cyclopentylidenemethyl, halophenyl (chlorophenyl), $C_1$- or $C_2$-alkoxyphenyl (ethoxyphenyl) or $C_1$–$C_4$-alkylphenyl (tert-butylphenyl), X is straight-chain or branched, saturated or unsaturated $C_1$–$C_{12}$-alkylene which is unsubstituted or substituted by halogen or hydroxyl, and n is 0 or 1, have an excellent fungicidal action.

The radicals stated in the general formula I may have the following meanings: $R^1$ is, for example, $C_1$–$C_3$-alkyl, such as methyl, ethyl or isopropyl, and $R^2$ may be, for example, hydrogen, methyl, ethyl, propyl, butyl, methoxy, ethoxy, isopropoxy or butoxy.

$R^3$ may be, for example, hydrogen, halogen (e.g. fluorine, chlorine or bromine), cyano, aryl (phenyl or naphthyl) or aryloxy (phenoxy), the aromatic ring being unsubstituted or substituted by one or more of the following radicals: $C_1$–$C_6$-alkyl (e.g. methyl, ethyl, n-propyl, isopropyl, n-butyl, isobutyl, sec-butyl or tert-butyl, N-pentyl, isopentyl, sec-pentyl, tert-pentyl or neopentyl or hexyl), $C_2$–$C_4$-alkenyl (e.g. vinyl or allyl), $C_1$- or $C_2$-haloalkyl (e.g. difluoromethyl or trifluoromethyl), $C_1$–$C_6$-alkoxy (e.g. methoxy, ethoxy, isopropoxy or tert-butoxy), $C_1$–$C_4$-alkoxy-$C_1$–$C_4$-alkyl (e.g.methoxymethyl), aryl-$C_1$- or -$C_2$-alkyl (e.g. benzyl), aryloxy (e.g. phenoxy), aryloxy-$C_1$–$C_4$-alkyl (e.g. phenoxymethyl or phenoxyethyl), aryloxy-$C_1$–$C_4$-alkoxy, haloaryloxy-$C_1$–$C_4$-alkoxy (e.g. phenoxymethoxy, phenoxyethoxy, phenoxypropoxy, 2-chlorophenoxyethoxy or 4-chlorophenoxyethoxy), halogen (e.g. fluorine, chlorine, bromine or iodine), halogen-$C_1$–$C_4$-alkoxy (e.g. 1,1,2,2-tetrafluoroethoxy), $C_1$–$C_4$-alkylthio (e.g. methylthio), thiocyanato, cyano or nitro.

$R^3$ may furthermore be hetaryl (e.g. furyl, pyrrolyl, piperidinyl or morpholinyl), $C_3$–$C_7$-cycloalkyl, $C_5$- or $C_6$-cycloalkenyl (e.g. cyclopropyl, cyclobutyl, cyclopentyl, cyclopentenyl, cyclohexyl, cyclohexenyl or cycloheptyl), 1-adamantyl, 9-fluorenyl or a substituted cyclohexyl radical (1-methylcyclohexyl) or a cyclopropyl radical which is substituted by $C_1$–$C_4$-alkyl (e.g. methyl or ethyl), halogen (chlorine or bromine), $C_1$- or $C_2$-haloalkyl (trifluoromethyl, tetrabromoethyl or dichlorodibromoethyl), $C_3$- or $C_4$-alkenyl (methylvinyl or dimethylvinyl), $C_2$–$C_4$-haloalkenyl (dichlorovinyl, dichlorobutadienyl, difluorovinyl or trifluoromethylvinyl), methoxycarbonyl-$C_3$- or -$C_4$-alkenyl (methylmethoxycarbonylvinyl), cyclopentylidenemethyl, halophenyl (chlorophenyl), $C_1$- or $C_2$-alkoxyphenyl (ethoxyphenyl) or $C_1$–$C_4$-alkylphenyl (tertbutylphenyl), for example 2,2-dimethyl-3-(2',2', -dimethylvinyl)-cyclopropyl (A1), 2,2-dimethyl-3-(2',2'-dichlorovinyl)-cyclopropyl (A2), 2,2-dimethyl-3-(2',2'-dibromovinyl)-cyclopropyl (A3), 2,2-dimethyl-3-(2'-trifluoromethyl-2'-chlorovinyl)-cyclopropyl (A4), 2,2-dichloro-3,3-dimethylcyclopropyl (A5), 2,2,3,3-tetramethylcyclopropyl (A6), 2,2-dimethyl-3-(2',2'-difluorovinyl)-cyclopropyl (A7), 2,2-dimethyl-3-(2'-trifluoromethyl-2'-fluorovinyl)-cyclopropyl (A8), 2,2-dimethyl-3-(2'-methyl-2'-methoxycarbonylvinyl)-cyclopropyl (A9), 2,2-dimethyl-3-(4',4'-dichlorobutadienyl)-cyclopropyl (A10), 2,2-dimethyl-3-(1'-bromo-2',2',2'-tribromoethyl)-cyclopropyl (A11), 2,2-dimethyl-3-(1'-bromo-2',2'-dichloro-2'-bromoethyl)-cyclopropyl (A12), 1-(2',4'-dichlorophenyl)-cyclopropyl (A13), 1-(4'-chlorophenyl)-cyclopropyl (A14), 1-(4'-ethoxyphenyl)-2,2-dichlorocyclopropyl (A15), 2,2-dimethyl-3-(4'-tert-butylphenyl)-cyclopropyl (A16) and 1-methyl-2,2-dichlorocyclopropyl (A17), and X may be for example, a straight-chain $C_1$–$C_{12}$-alkylene radical (e.g. methylene, ethylene, propylene, butylene, pentylene, hexylene or heptylene), a branched $C_1$–$C_{12}$-alkylene radical (e.g. methylmethylene, dimethylmethylene, ethylmethylene, n- or isopropylmethylene, methylethylene, methylpropylene, dimethylpropylene, ethylpropylene, methylbutylene, dimethylbutylene, ethylbutylene, n- or isopropylbutylene, methylpentylene, dimethylpentylene, trimethylpentylene, methylhexylene, dimethylhexylene, trimethylhexylene, ethylhexylene, n- or isopropylhexylene or methylheptylene), a $C_2$–$C_8$-alkenylene radical (e.g. vinylene, allylene, methylallylene, butenylene or methylbutenylene), a halogen-substituted $C_1$–$C_{12}$-alkylene radical (e.g. chloromethylene, dichloromethylene, fluoromethylene, difluoromethylene, bromomethylene, dibromomethylene, chloroethylene, fluoroethylene, bromoethylene, fluoropropylene, chloropropylene, bromopropylene, fluorobutylene, chlorobutylene or bromobutylene), a halogen-substituted $C_2$–$C_4$-alkenylene radical (e.g. chlorovinylene or dichlorovinylene) or a hydroxyl-substituted $C_1$–$C_8$-alkylene radical (e.g. hydroxymethylene or hydroxyethylene).

Where n is 0, $X_n$ is a single bond.

Because of the C=C double bond, the novel compounds of the formula I are obtained in their preparation as E/Z isomer mixtures, which can be separated into the individual components in a conventional manner, for example by crystallization or chromatography. Both the individual isomeric compounds and their mixtures are embraced by the invention and can be used as fungicides.

The novel compounds of the formula I can be prepared, for example, by reacting an ortho-substituted benzyl bromide of the general formula III, where $R^1$ and $R^2$ have the abovementioned meanings, with an alkali metal salt, alkaline earth metal salt or ammonium salt of a carboxylic acid of the formula II, where $R^3$, X and n have the abovementioned meanings, in a solvent or diluent and with or without the addition of a catalyst to give the novel compounds.

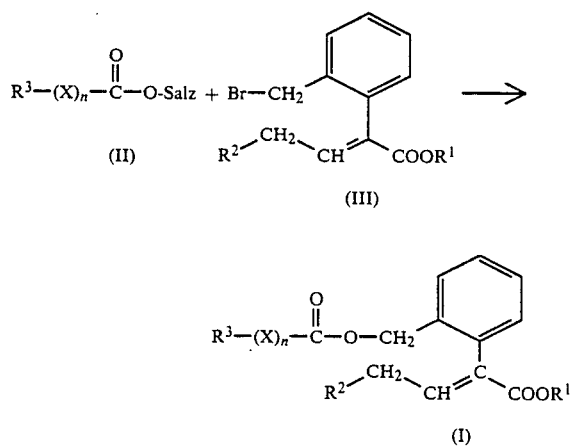

The preparation of carboxylic esters from alkyl halides and carboxylates is known (cf. for example Synthesis 1975, 805).

Examples of suitable solvents or diluents for the reaction of II with III are acetone, acetonitrile, dimethyl sulfoxide, dioxane, dimethylformamide, N-methylpyrrolidone, N,N'-dimethylpropyleneurea and pyridine.

It may also be advantageous to add a catalyst, e.g. potassium iodide or tetramethylethylenediamine, to the reaction mixture in an amount of from 0.01 to 10% by weight, based on compound III.

The corresponding reactions can also be carried out in a two-phase system (e.g. carbon tetrachloride/water). Examples of suitable phase transfer catalysts are trioctylpropylammonium chloride and cetyltrimethylammonium chloride (cf. Synthesis 1974, 867).

The carboxylates of the formula II are known. They can be prepared from the corresponding carboxylic acids using bases (e.g. potassium hydroxide) in an inert solvent (e.g. ethanol).

The ortho-substituted benzyl bromides of the formula III can be prepared by reacting a known α-ketocarboxylic ester of the formula IV (cf. for example J. M. Photis, Tetrahedron Lett. 1980, 3539)

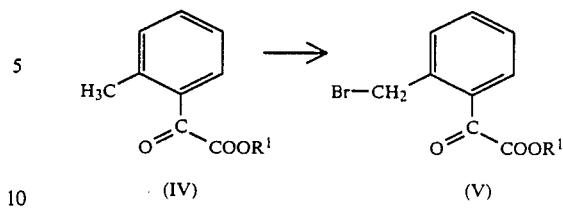

with bromine in a solvent, for example tetrachloromethane, with or without exposure to a light source (e.g. 300 W mercury vapor, or with N-bromosuccinimide (Horner and Winkelmann, Angew. Chem. 71 (1959), 349) to give the α-ketocarboxylic esters of the general formula V, $R^1$ having the abovementioned meanings.

The α-ketocarboxylic esters of the formula V can be converted into the abovementioned ortho-substituted benzyl bromides of the general formula III in a Wittig reaction with an alkyl- or alkoxymethyltriphenylphosphonium bromide in the presence of a base, e.g. n-butyllithium, sodium methylate, potassium tert-butylate or sodium hydride (cf. G. Wittig and U. Schöllkopf, Org. Synth., Coll. Vol. V (1973), 751–754).

The novel compounds of the formula I can be prepared, for example, by subjecting a novel α-ketocarboxylic ester of the general formula VI to a Wittig reaction with an alkyl- or alkoxymethyltriphenylphosphonium bromide in the presence of a base, e.g. n-butyllithium, sodium methylate, potassium tert-butylate or sodium hydride, $R^1$, $R^2$, $R^3$, X and n having the abovementioned meanings:

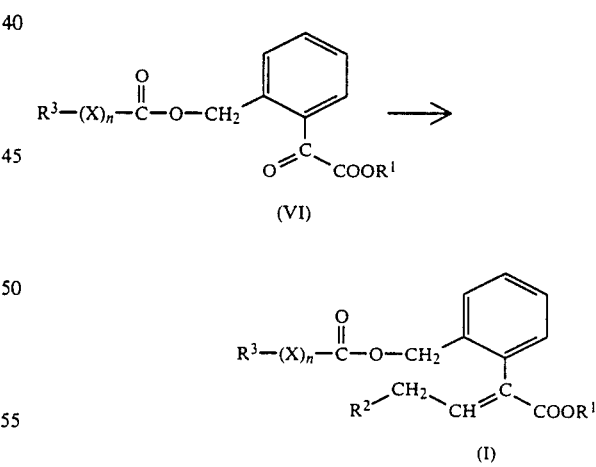

The novel α-ketocarboxylic esters of the formula VI are useful intermediates. They can be prepared, for example, by reacting the abovementioned compound of the formula V with an alkali metal salt, alkaline earth metal salt or ammonium salt of a carboxylic acid of the formula II, where $R^3$, $R^1$, X and n have the abovementioned meanings, in a solvent or diluent and with or without the addition of a catalyst, the product being a novel compound of the formula VI.

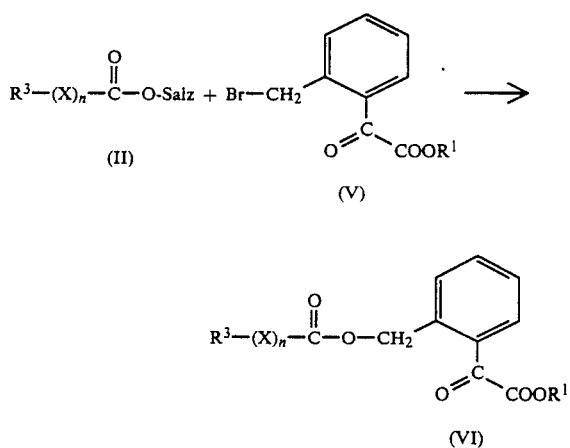

The preparation of carboxylic esters from alkyl halides and carboxylates is known (cf. for example Synthesis 1975, 805).

Suitable solvents or diluents for the reaction of II with V are acetone, acetonitrile, dimethyl sulfoxide, dioxane, dimethylformamide, N-methylpyrrolidone, N,N'-dimethylpropyleneurea and pyridine.

It may also be advantageous to add a catalyst, e.g. potassium iodide or tetramethylethylenediamine, to the reaction mixture in an amount of from 0.01 to 10% by weight, based on compound V.

The corresponding reactions can also be carried out in a two-phase system (e.g. carbon tetrachloride/water). Examples of suitable phase transfer catalysts are trioctylpropylammonium chloride and cetyltrimethylammonium chloride (cf. Synthesis 1974, 867).

The Examples which follow illustrate the preparation of the novel compounds of the formulae I and VI.

Method 1

Preparation of methyl 2-(bromomethyl)-phenylglyoxylate 5.34 g (30 millimoles) of methyl 2-methylphenylglyoxylate and 5.34 g (30 millimoles) of N-bromosuccinimide in 1,000 ml of tetrachloromethane are exposed to a 300 W mercury vapor lamp for one hour. Thereafter, the organic phase is washed once with water and three times with sodium bicarbonate solution, dried over sodium sulfate/sodium carbonate and evaporated down, and the crude product is then chromatographed over silica gel using 1:9 methyl tert-butyl ether/n-hexane. 3.8 g (49%) of the abovementioned compound are obtained as a yellow oil.

$^1$H-NMR (CDCl$_3$):δ=3.97 (s, 3H), 4.90 (s, 2H), 7.4–7.8 (m, 4H).

IR (film): 2955, 1740, 1689, 1435, 1318, 1207, 999 cm$^{-1}$)

Method 2

Preparation of methyl ortho-[2,2-dimethyl-3-(2',2'-dichlorovinyl)-cyclopropylcarboxymethylene]-phenylglyoxylate 53.4 g (0.3 mole) of methyl 2-methylphenylglyoxylate and 58.7 g (0.33 mole) of N-bromosuccinimide in 3,000 ml of tetrachloromethane are exposed to a 300 W mercury vapor lamp for 1.5 hours. Thereafter, the solution is evaporated down to one third, washed with water, dried over Na$_2$SO$_4$ and evaporated down. The residue is dissolved in 500 ml of N-methyl-2-pyrrolidone, 49.4 g (0.2 mole) of potassium 2,2-dimethyl-3-(2'2'-dichlorovinyl)-cyclopropylcarboxylate and a pinch of potassium iodide are added and stirring is carried out for 16 hours at room temperature (21° C.). The mixture is then poured onto water and extracted thoroughly with methyl tert-butyl ether. The combined organic phases are washed with water, dried over sodium sulfate and evaporated down. The crude product is chromatographed over a silica gel column (5:1 hexane/methyl tert-butyl ether). 40 g (52%) of the abovementioned ester are obtained as an oil (cis/trans isomerism of the three-membered ring).

$^1$H-NMR (CDCl$_3$):δ=1.22/1.30 (2s, 3H), 1.31/1.35 (2s, 3H), 1.70/1.95 (2d, 1H), 2.10/2.28 (2t, 1H), 4.0 (s, 3H), 5.48/5.51 (2s, 1H), 5.65/6.25 (2d, 1H), 7.4–7.8 (m, 4H).

EXAMPLE 1

Preparation of methyl α-[ortho-(2,2-dimethyl-3-(2',2'-dichlorovinyl)-cyclopropylcarboxymethylene)-phenyl]-β-methylacrylate (compound No. 286)

11.3 g (27 millimoles) of ethyltriphenylphosphonium bromide in 100 ml of absolute tetrahydrofuran are initially taken under nitrogen. 10.8 ml (27 millimoles) of a 2.5 molar solution of n-butyllithium in hexane are added dropwise at 0° C. Stirring is carried out for one hour at 0° C., after which 8 g (21 millimoles) of methyl ortho-[2,2-dimethyl-3-(2',2'-dichlorovinyl)-cyclopropylcarboxymethylene]-phenylglyoxylate dissolved in 40 ml of absolute tetrahydrofuran are added dropwise at −78° C. The mixture is warmed up slowly to room temperature (21° C.) and is poured onto saturated ammonium chloride solution. It is then extracted several times with methyl tert-butyl ether and the organic phase is washed with water, dried over sodium sulfate and evaporated down. The crude product is purified by chromatography over a silica gel column (1:2 methyl tert-butyl ether/n-hexane). 4 g (48%) of the abovementioned ester are obtained as an oil (cis/trans isomerism of the three-membered ring).

$^{13}$C-NMR (CDCl$_3$):δ=14.99/20.13, 15.37, 22.59/28.40, 27.40/28.90, 31.89/34.91, 32.67/32.98, 51.90, 64.31/64.59, 121.03/122.93, 124.93/126.97, 128.09, 128.25, 128.93, 130.31, 133.56, 134.75, 135.11, 141.25, 166.98, 170.07/ 170.67.

The compounds listed in the Table below are prepared in a similar manner.

TABLE 1

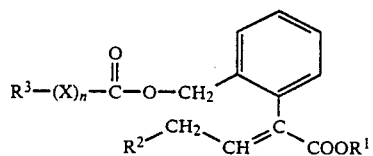
(I)

| No. | R³ | (X)ₙ | R² | R¹ | mp (°C.) IR (cm⁻¹) |
|---|---|---|---|---|---|
| 1 | H | —CH₂— | H | CH₃ | |
| 2 | H | —CH₂—CH₂— | H | CH₃ | |
| 3 | H | —CH₂—CH(CH₃)— | H | CH₃ | |
| 4 | H | —CH₂—C(CH₃)— | H | CH₃ | oil 1721, 1253, 1149, 760 |
| 5 | H | —CH=CH— | H | CH₃ | |
| 6 | H | —CH=C(CH₃)— | H | CH₃ | |
| 7 | H | —C≡C— | H | CH₃ | |
| 8 | H | —CH₂—CH₂—CH₂— | H | CH₃ | |
| 9 | H | —CH₂—CH₂—CH(CH₃)— | H | CH₃ | |
| 10 | H | —CH₂—CH(CH₃)—CH₂— | H | CH₃ | |
| 11 | H | —CH₂—CH₂—C(CH₃)₂— | H | CH₃ | |
| 12 | H | —CH₂—C(CH₃)₂—CH₂— | H | CH₃ | |
| 13 | H | —CH₂—CH₂—C(C₂H₅)₂— | H | CH₃ | |
| 14 | H | —CH=CH—CH₂— | H | CH₃ | |
| 15 | H | —CH₂—CH=CH— | H | CH₃ | |
| 16 | H | —CH₂—C(CH₃)=CH— | H | CH₃ | |
| 17 | H | —CH₂—CH=C(CH₃)— | H | CH₃ | |
| 18 | H | —(CH₂)₄— | H | CH₃ | |
| 19 | H | —CH₂—CH₂—CH₂—CH(CH₃)— | H | CH₃ | |
| 20 | H | —CH₂—CH₂—CH(CH₃)—CH₂— | H | CH₃ | |
| 21 | H | —(CH₂)₃—C(CH₃)₂— | H | CH₃ | |
| 22 | H | —(CH₂)₃—CH(C₂H₅)— | H | CH₃ | |
| 23 | H | —(CH₂)₃—CH(n-C₃H₇)— | H | CH₃ | |
| 24 | H | —CH₂—CH=CH—CH₂— | H | CH₃ | |
| 25 | H | —CH₂—C(CH₃)=CH—CH₂— | H | CH₃ | |
| 26 | H | —(CH₂)₅— | H | CH₃ | |
| 27 | H | —(CH₂)₄—CH(CH₃)— | H | CH₃ | |
| 28 | H | —(CH₂)₄—CH(C₂H₅)— | H | CH₃ | |
| 29 | H | —(CH₂)₃—CH(CH₃)—CH₂— | H | CH₃ | |
| 30 | H | —CH₂—CH=CH—CH=CH— | H | CH₃ | |
| 31 | H | —CH₂—C(CH₃)=CH—CH=CH— | H | CH₃ | |
| 32 | H | —(CH₂)₆— | H | CH₃ | |
| 33 | H | —(CH₂)₅—CH(CH₃)— | H | CH₃ | |
| 34 | H | —(CH₂)₄—CH(CH₃)—CH₂— | H | CH₃ | |
| 35 | H | —(CH₂)₅—CH(n-C₃H₇)— | H | CH₃ | |
| 36 | H | —(CH₂)₇— | H | CH₃ | |
| 37 | H | —(CH₂)₆—CH(CH₃)— | H | CH₃ | |
| 38 | H | —(CH₂)₅—CH(CH₃)—CH₂— | H | CH₃ | |
| 39 | H | —(CH₂)₆—C(CH₃)₂— | H | CH₃ | |
| 40 | H | —(CH₂)₈— | H | CH₃ | |
| 41 | H | —(CH₂)₉— | H | CH₃ | |
| 42 | H | —(CH₂)₁₀— | H | CH₃ | |
| 43 | H | —CHCl— | H | CH₃ | |
| 44 | H | —CCl₂— | H | CH₃ | |
| 45 | Cl | —CCl₂— | H | CH₃ | |
| 46 | H | —CHBr— | H | CH₃ | |
| 47 | H | —CBr₂— | H | CH₃ | |
| 48 | Br | —CBr₂— | H | CH₃ | |
| 49 | H | —CHF— | H | CH₃ | |
| 50 | H | —CF₂— | H | CH₃ | |
| 51 | F | —CF₂— | H | CH₃ | |
| 52 | H | —CH=CCl— | H | CH₃ | |
| 53 | H | —CCl=CCl— | H | CH₃ | |
| 54 | Cl | —C(CH₃)₂— | H | CH₃ | |
| 55 | H | —C(CH₃)₂— | H | CH₃ | |
| 56 | H | —CHCl—CH(CH₃)— | H | CH₃ | |
| 57 | H | —CHCl—C(CH₃)₂— | H | CH₃ | |
| 58 | H | —CHBr—CH(CH₃)— | H | CH₃ | |
| 59 | Br | —C(C₂H₅)₂— | H | CH₃ | |
| 60 | H | —CH(OH)— | H | CH₃ | |
| 61 | H | —CH₂—CH(OH)— | H | CH₃ | |
| 62 | H | —CH₂—CH₂—CH(OH)— | H | CH₃ | |
| 63 | H | —CH₂—CH(OH)—CH₂— | H | CH₃ | |
| 64 | H | —CH(OH)—CH₂— | H | CH₃ | |
| 65 | H | —CH(OH)—C(CH₃)₂— | H | CH₃ | |
| 66 | H | —CH₂—C(OH)(CH₃)— | H | CH₃ | |
| 67 | H | —CH₂—CH(CH₃)—CH(OH)— | H | CH₃ | |
| 68 | H | —CH=CH—CH(OH)— | H | CH₃ | |
| 69 | H | —CH=CH—CH₂—CH(OH)— | H | CH₃ | |
| 70 | CN | —CH₂— | H | CH₃ | |
| 71 | cyclopropyl | — | H | CH₃ | oil 1721, 1390, 1256, 1170, 760 |

TABLE 1-continued

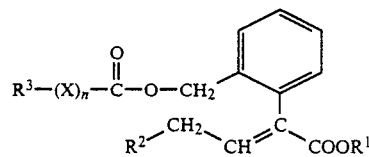
(I)

| No. | R³ | (X)ₙ | R² | R¹ | mp (°C.) IR (cm⁻¹) |
|---|---|---|---|---|---|
| 72 | cyclobutyl | — | H | $CH_3$ | |
| 73 | cyclopentyl | — | H | $CH_3$ | |
| 74 | cyclohexyl | — | H | $CH_3$ | |
| 75 | adamantyl | — | H | $CH_3$ | |
| 76 | 9-fluorenyl | — | H | $CH_3$ | |
| 77 | cyclopentyl | —$CH_2$— | H | $CH_3$ | |
| 78 | 3-cyclopentenyl | —$CH_2$— | H | $CH_3$ | |
| 79 | cyclohexyl | —$CH_2$— | H | $CH_3$ | |
| 80 | cyclopentyl | —$CH_2$—$CH_2$— | H | $CH_3$ | |
| 81 | cyclohexyl | —$CH_2$—$CH_2$— | H | $CH_3$ | |
| 82 | cyclohexyl | —$(CH_2)_3$— | H | $CH_3$ | |
| 83 | $C_6H_5$ (= phenyl) | — | H | $CH_3$ | oil 1719, 1271, 713 |
| 84 | 2-$CH_3$—$C_6H_4$ | — | H | $CH_3$ | |
| 85 | 3-$CH_3$—$C_6H_4$ | — | H | $CH_3$ | |
| 86 | 4-$CH_3$—$C_6H_4$ | — | H | $CH_3$ | |
| 87 | 2,3-$(CH_3)_2$—$C_6H_3$ | — | H | $CH_3$ | |
| 88 | 2,4-$(CH_3)_2$—$C_6H_3$ | — | H | $CH_3$ | |
| 89 | 2,6-$(CH_3)_2$—$C_6H_3$ | — | H | $CH_3$ | |
| 90 | 3,4-$(CH_3)_2$—$C_6H_3$ | — | H | $CH_3$ | |
| 91 | 3,5-$(CH_3)_2$—$C_6H_3$ | — | H | $CH_3$ | |
| 92 | 2,4,6-$CH_3)_2$—$C_6H_2$ | — | H | $CH_3$ | |
| 93 | 4-t-$C_4H_9$—$C_6H_4$ | — | H | $CH_3$ | |
| 94 | 2-$C_6H_5$—$C_6H_4$ | — | H | $CH_3$ | |
| 95 | 4-$C_6H_5$—$C_6H_4$ | — | H | $CH_3$ | |
| 96 | 2-benzyl-$C_6H_4$ | — | H | $CH_3$ | |
| 97 | 4-benzyl-$C_6H_4$ | — | H | $CH_3$ | |
| 98 | 2-Cl—$C_6H_4$ | — | H | $CH_3$ | |
| 99 | 3-Cl—$C_6H_4$ | — | H | $CH_3$ | |
| 100 | 4-Cl—$C_6H_4$ | — | H | $CH_3$ | |
| 101 | 2,4-$Cl_2$—$C_6H_3$ | — | H | $CH_3$ | |
| 102 | 2,5-$Cl_2$—$C_6H_3$ | — | H | $CH_3$ | |
| 103 | 2,6-$Cl_2$—$C_6H_3$ | — | H | $CH_3$ | |
| 104 | 3,4-$Cl_2$—$C_6H_3$ | — | H | $CH_3$ | |
| 105 | 3,5-$Cl_2$—$C_6H_3$ | — | H | $CH_3$ | |
| 106 | 2,4,5-$Cl_3$—$C_6H_2$ | — | H | $CH_3$ | |
| 107 | 2,3,4,5,6-$Cl_5$—$C_6$ | — | H | $CH_3$ | |
| 108 | 2-F,4-Cl—$C_6H_3$ | — | H | $CH_3$ | |
| 109 | 2-F-$C_6H_4$ | — | H | $CH_3$ | |
| 110 | 3-F-$C_6H_4$ | — | H | $CH_3$ | |
| 111 | 4-F-$C_6H_4$ | — | H | $CH_3$ | |
| 112 | 2,4-$F_2$—$C_6H_3$ | — | H | $CH_3$ | |
| 113 | 2,6-$F_2$—$C_6H_3$ | — | H | $CH_3$ | |
| 114 | 2,3,4,5,6-$F_5$—$C_6$ | — | H | $CH_3$ | |
| 115 | 2-$CF_3$—$C_6H_4$ | — | H | $CH_3$ | |
| 116 | 3-$CF_3$—$C_6H_4$ | — | H | $CH_3$ | |
| 117 | 4-$CF_3$—$C_6H_4$ | — | H | $CH_3$ | |
| 118 | 2-$OCH_3$—$C_6H_4$ | — | H | $CH_3$ | |
| 119 | 3-$OCH_3$—$C_6H_4$ | — | H | $CH_3$ | |
| 120 | 4-$OCH_3$—$C_6H_4$ | — | H | $CH_3$ | |
| 121 | 2-phenoxy-$C_6H_4$ | — | H | $CH_3$ | |
| 122 | 3-phenoxy-$C_6H_4$ | — | H | $CH_3$ | |
| 123 | 4-phenoxy-$C_6H_4$ | — | H | $CH_3$ | |
| 124 | 4-ethoxy-$C_6H_4$ | — | H | $CH_3$ | |
| 125 | 2-phenoxyethoxy-$C_6H_4$ | — | H | $CH_3$ | |
| 126 | 2-(2'-Cl-phenoxyethoxy)-$C_6H_4$ | — | H | $CH_3$ | |
| 127 | 2-(3'-Cl-phenoxyethoxy)-$C_6H_4$ | — | H | $CH_3$ | |
| 128 | 2-(4'-Cl-phenoxyethoxy)-$C_6H_4$ | — | H | $CH_3$ | |
| 129 | 3-phenoxyethoxy-$C_6H_4$ | — | H | $CH_3$ | |
| 130 | 3-(4'-Cl-phenoxyethoxy)-$C_6H_4$ | — | H | $CH_3$ | |
| 131 | 4-phenoxyethoxy-$C_6H_4$ | — | H | $CH_3$ | |
| 132 | 2-phenoxypropoxy-$C_6H_4$ | — | H | $CH_3$ | |
| 133 | 3-phenoxypropoxy-$C_6H_4$ | — | H | $CH_3$ | |
| 134 | 4-phenoxypropoxy-$C_6H_4$ | — | H | $CH_3$ | |
| 135 | $C_6H_5$ | —$CH_2$— | H | $CH_3$ | |
| 136 | 2-$CH_3$—$C_6H_4$ | —$CH_2$— | H | $CH_3$ | |
| 137 | $C_6H_5$ | —$CH(CH_3)$— | H | $CH_3$ | |
| 138 | 4-phenyl-$C_6H_4$ | —$CH_2$— | H | $CH_3$ | |
| 139 | 2-F—$C_6H_4$ | —$CH_2$— | H | $CH_3$ | |
| 140 | 3-F—$C_6H_4$ | —$CH_2$— | H | $CH_3$ | |
| 141 | 4-F—$C_6H_4$ | —$CH_2$— | H | $CH_3$ | |
| 142 | 2-Cl—$C_6H_4$ | —$CH_2$— | H | $CH_3$ | |
| 143 | 3-Cl—$C_6H_4$ | —$CH_2$— | H | $CH_3$ | |

TABLE 1-continued

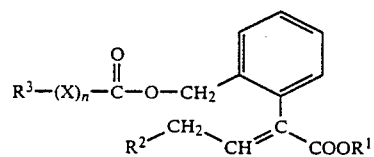

(I)

| No. | R³ | (X)ₙ | R² | R¹ | mp (°C.) IR (cm⁻¹) |
|---|---|---|---|---|---|
| 144 | 4-Cl—C₆H₄ | —CH₂— | H | CH₃ | |
| 145 | 2,4-Cl₂—C₆H₃ | —CH₂— | H | CH₃ | |
| 146 | 2,6-Cl₂—C₆H₃ | —CH₂— | H | CH₃ | |
| 147 | 2-Cl,4-F—C₆H₃ | —CH₂— | H | CH₃ | |
| 148 | 2-ethoxy-C₆H₄ | —CH₂— | H | CH₃ | |
| 149 | 4-ethoxy-C₆H₄ | —CH₂— | H | CH₃ | |
| 150 | 2-OCH₃—C₆H₄ | —CH₂— | H | CH₃ | |
| 151 | 4-OCH₃—C₆H₄ | —CH₂— | H | CH₃ | |
| 152 | 4-t-C₄H₉—C₆H₄ | —CH₂— | H | CH₃ | |
| 153 | C₆H₅ | —CH(iso-C₃H₇)— | H | CH₃ | |
| 154 | 4-Cl—C₆H₄ | —CH(iso-C₃H₇)— | H | CH₃ | |
| 155 | 4-F—C₆H₄ | —CH(iso-C₃H₇)— | H | CH₃ | |
| 156 | 4-OCF₂H—C₆H₄ | —CH(iso-C₃H₇)— | H | CH₃ | |
| 157 | C₆H₅ | —CH(OH)— | H | CH₃ | |
| 158 | 2-OCH₃—C₆H₄ | —CH(OH)— | H | CH₃ | |
| 159 | 3-OCH₃—C₆H₄ | —CH(OH)— | H | CH₃ | |
| 160 | 4-OCH₃—C₆H₄ | —CH(OH)— | H | CH₃ | |
| 161 | 4-Cl—C₆H₄ | —CH(OH)— | H | CH₃ | |
| 162 | C₆H₅ | —CH(CH₂OH)— | H | CH₃ | |
| 163 | C₆H₅ | —CH₂—CH₂— | H | CH₃ | |
| 164 | C₆H₅ | —CH(CH₃)—CH₂— | H | CH₃ | |
| 165 | C₆H₅ | —CH₂—CH(CH₃)— | H | CH₃ | |
| 166 | C₆H₅ | —CH(CH₃)—CH(CH₃)— | H | CH₃ | |
| 167 | C₆H₅ | —CH(C₆H₅)—CH₂— | H | CH₃ | |
| 168 | 4-t-C₄H₉—C₆H₄ | —CH₂—CH₂— | H | CH₃ | |
| 169 | 4-t-C₄H₉—C₆H₄ | —CH₂—CH(CH₃)— | H | CH₃ | |
| 170 | 2-Cl—C₆H₄ | —CH₂—CH₂— | H | CH₃ | |
| 171 | 3-Cl—C₆H₄ | —CH₂—CH₂— | H | CH₃ | |
| 172 | 4-Cl—C₆H₄ | —CH₂—CH₂— | H | CH₃ | |
| 173 | 2-F—C₆H₄ | —CH₂—CH₂— | H | CH₃ | |
| 174 | 3-F—C₆H₄ | —CH₂—CH₂— | H | CH₃ | |
| 175 | 4-F—C₆H₄ | —CH₂—CH₂— | H | CH₃ | |
| 176 | 2-OCH₃—C₆H₄ | —CH₂—CH₂— | H | CH₃ | |
| 177 | 4-OCH₃—C₆H₄ | —CH₂—CH₂— | H | CH₃ | |
| 178 | C₆H₅ | —CH=CH— | H | CH₃ | oil 1716, 1637, 1254, 1164, 768 |
| 179 | 2-Cl—C₆H₄ | —CH=CH— | H | CH₃ | |
| 180 | 3-Cl—C₆H₄ | —CH=CH— | H | CH₃ | |
| 181 | 4-Cl—C₆H₄ | —CH=CH— | H | CH₃ | |
| 182 | 2,6-Cl₂—C₆H₃ | —CH=CH— | H | CH₃ | |
| 183 | 2,4-Cl₂—C₆H₃ | —CH=CH— | H | CH₃ | |
| 184 | 2-F—C₆H₄ | —CH=CH— | H | CH₃ | |
| 185 | 3-F—C₆H₄ | —CH=CH— | H | CH₃ | |
| 186 | 4-F—C₆H₄ | —CH=CH— | H | CH₃ | |
| 187 | 2-CF₃—C₆H₄ | —CH=CH— | H | CH₃ | |
| 188 | 4-CF₃—C₆H₄ | —CH=CH— | H | CH₃ | |
| 189 | 2-CH₃—C₆H₄ | —CH=CH— | H | CH₃ | |
| 190 | 4-CH₃—C₆H₄ | —CH=CH— | H | CH₃ | |
| 191 | 4-i-C₃H₇—C₆H₄ | —CH=CH— | H | CH₃ | |
| 192 | 4-t-C₄H₉—C₆H₄ | —CH=CH— | H | CH₃ | |
| 193 | 2-OCH₃—C₆H₄ | —CH=CH— | H | CH₃ | |
| 194 | 3-OCH₃—C₆H₄ | —CH=CH— | H | CH₃ | |
| 195 | 4-OCH₃—C₆H₄ | —CH=CH— | H | CH₃ | |
| 196 | 2-phenoxy-C₆H₄ | —CH=CH— | H | CH₃ | |
| 197 | 3-phenoxy-C₆H₄ | —CH=CH— | H | CH₃ | |
| 198 | 4-phenoxy-C₆H₄ | —CH=CH— | H | CH₃ | |
| 199 | C₆H₅ | —(CH₂)₃— | H | CH₃ | |
| 200 | C₆H₅ | —CH(CH₃)—CH₂—CH₂— | H | CH₃ | |
| 201 | C₆H₅ | —CH₂—CH(CH₃)—CH₂— | H | CH₃ | |
| 202 | C₆H₅ | —CH₂—CH₂—CH(CH₃)— | H | CH₃ | |
| 203 | 2-Cl—C₆H₄ | —(CH₂)₃— | H | CH₃ | |
| 204 | 4-Cl—C₆H₄ | —(CH₂)₃— | H | CH₃ | |
| 205 | 2-OCH₃—C₆H₄ | —(CH₂)₃— | H | CH₃ | |
| 206 | 4-OCH₃—C₆H₄ | —(CH₂)₃— | H | CH₃ | |
| 207 | 4-t-C₄H₉—C₆H₄ | —(CH₂)₃— | H | CH₃ | |
| 208 | C₆H₅ | —CH=CH—CH₂— | H | CH₃ | |
| 209 | C₆H₅ | —(CH₂)₄— | H | CH₃ | |
| 210 | 2-Cl—C₆H₄ | —(CH₂)₄— | H | CH₃ | |
| 211 | 4-Cl—C₆H₄ | —(CH₂)₄— | H | CH₃ | |
| 212 | 2-OCH₃—C₆H₄ | —(CH₂)₄— | H | CH₃ | |
| 213 | 4-OCH₃—C₆H₄ | —(CH₂)₄— | H | CH₃ | |
| 214 | 4-CF₃—C₆H₄ | —(CH₂)₄— | H | CH₃ | |

TABLE 1-continued

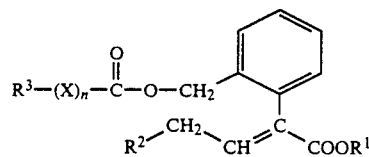
(I)

| No. | R³ | (X)ₙ | R² | R¹ | mp (°C.) IR (cm⁻¹) |
|---|---|---|---|---|---|
| 215 | 2-CH₃—C₆H₄ | —(CH₂)₄— | H | CH₃ | |
| 216 | 4-CH₃—C₆H₄ | —(CH₂)₄— | H | CH₃ | |
| 217 | C₆H₅ | —CH₂—CH₂—CH(CH₃)—CH₂— | H | CH₃ | |
| 218 | C₆H₅ | —(CH₂)₅— | H | CH₃ | |
| 219 | 2-CH₃—C₆H₄ | —(CH₂)₅— | H | CH₃ | |
| 220 | 4-CH₃—C₆H₄ | —(CH₂)₅— | H | CH₃ | |
| 221 | 2-Cl—C₆H₄ | —(CH₂)₅— | H | CH₃ | |
| 222 | 4-Cl—C₆H₄ | —(CH₂)₅— | H | CH₃ | |
| 223 | 2-OCH₃—C₆H₄ | —(CH₂)₅— | H | CH₃ | |
| 224 | 4-OCH₃—C₆H₄ | —(CH₂)₅— | H | CH₃ | |
| 225 | 4-CF₃—C₆H₄ | —(CH₂)₅— | H | CH₃ | |
| 226 | C₆H₅ | —CH₂—CH₂—CH₂—CH(CH₃)—CH₂— | H | CH₃ | |
| 227 | C₆H₅ | —CH₂—CH(CH₃)—CH₂—CH(CH₃)—CH₂— | H | CH₃ | |
| 228 | 4-t-C₄H₉—C₆H₄ | —CH₂—CH(CH₃)—CH₂—CH(CH₃)—CH₂— | H | CH₃ | |
| 229 | C₆H₅ | —(CH₂)₆— | H | CH₃ | |
| 230 | C₆H₅ | —(CH₂)₄—CH(CH₃)—CH₂— | H | CH₃ | |
| 231 | C₆H₅—O— | —CH₂— | H | CH₃ | |
| 232 | 2-Cl—C₆H₄—O— | —CH₂— | H | CH₃ | |
| 233 | 3-Cl—C₆H₄—O— | —CH₂— | H | CH₃ | |
| 234 | 4-Cl—C₆H₄—O— | —CH₂— | H | CH₃ | |
| 235 | 2,4-Cl₂—C₆H₃—O— | —CH₂— | H | CH₃ | |
| 236 | 2-CH₃—C₆H₄—O— | —CH₂— | H | CH₃ | |
| 237 | 4-CH₃—C₆H₄—O— | —CH₂— | H | CH₃ | |
| 238 | 2-OCH₃—C₆H₄—O— | —CH₂— | H | CH₃ | |
| 239 | 4-OCH₃—C₆H₄—O— | —CH₂— | H | CH₃ | |
| 240 | 4-CF₃—C₆H₄—O— | —CH₂— | H | CH₃ | |
| 241 | C₆H₅—O— | —CH(CH₃)— | H | CH₃ | |
| 242 | C₆H₅—O— | —CH₂—CH₂— | H | CH₃ | |
| 243 | 2-Cl—C₆H₄—O— | —CH₂—CH₂— | H | CH₃ | |
| 244 | 4-Cl—C₆H₄—O— | —CH₂—CH₂— | H | CH₃ | |
| 245 | 2-CH₃—C₆H₄—O— | —CH₂—CH₂— | H | CH₃ | |
| 246 | 4-CH₃—C₆H₄—O— | —CH₂—CH₂— | H | CH₃ | |
| 247 | 2-OCH₃—C₆H₄—O— | —CH₂—CH₂— | H | CH₃ | |
| 248 | 4-OCH₃—C₆H₄—O— | —CH₂—CH₂ | H | CH₃ | |
| 249 | 4-t-C₄H₉—C₆H₄—O— | —CH₂—CH₂— | H | CH₃ | |
| 250 | 4-sec.-C₄H₉—C₆H₄—O— | —CH₂—CH₂— | H | CH₃ | |
| 251 | C₆H₅—O— | —(CH₂)₃— | H | CH₃ | |
| 252 | 2-Cl—C₆H₄—O— | —(CH₂)₃— | H | CH₃ | |
| 253 | 4-Cl—C₆H₄—O— | —(CH₂)₃— | H | CH₃ | |
| 254 | 3-Fl—C₆H₄—O— | —(CH₂)₃— | H | CH₃ | |
| 255 | 4-F—C₆H₄—O— | —(CH₂)₃— | H | CH₃ | |
| 256 | 2-CH₃—C₆H₄—O— | —(CH₂)₃— | H | CH₃ | |
| 257 | 4-CH₃—C₆H₄—O— | —(CH₂)₃— | H | CH₃ | |
| 258 | 2-OCH₃—C₆H₄—O— | —(CH₂)₃— | H | CH₃ | |
| 259 | 4-OCH₃—C₆H₄—O— | —(CH₂)₃— | H | CH₃ | |
| 260 | 2,4-Cl₂—C₆H₃—O— | —(CH₂)₃— | H | CH₃ | |
| 261 | 4-Cl—C₆H₄—O— | —CH(CH₃)—CH₂—CH₂— | H | CH₃ | |
| 262 | 2-CF₃—C₆H₄—O— | —(CH₂)₃— | H | CH₃ | |
| 263 | 3-CF₃—C₆H₄—O— | —(CH₂)₃— | H | CH₃ | |
| 264 | 4-CF₃—C₆H₄—O— | —(CH₂)₃— | H | CH₃ | |
| 265 | 4-t-butoxy-C₆H₄—O— | —(CH₂)₃— | H | CH₃ | |
| 266 | 2-CH₃,4-Cl—C₆H₃—O— | —(CH₂)₃— | H | CH₃ | |
| 267 | 4-C₂H₅—C₆H₄—O— | —(CH₂)₃— | H | CH₃ | |
| 268 | 4-iso-C₃H₇—C₆H₄—O— | —(CH₂)₃— | H | CH₃ | |
| 269 | 4-t-C₄H₉—C₆H₄—O— | —(CH₂)₃— | H | CH₃ | |
| 270 | C₆H₅—O— | —CH₂—CH(CH₃)—CH₂— | H | CH₃ | |
| 271 | C₆H₅—O— | —(CH₂)₄— | H | CH₃ | |
| 272 | 2-Cl—C₆H₄—O— | —(CH₂)₄— | H | CH₃ | |
| 273 | 4-Cl—C₆H₄—O— | —(CH₂)₄— | H | CH₃ | |
| 274 | 2,4-Cl₂—C₆H₃—O— | —(CH₂)₄— | H | CH₃ | |
| 275 | 2,6-Cl₂—C₆H₃—O— | —(CH₂)₄— | H | CH₃ | |
| 276 | 2-CH₃—C₆H₄—O— | —(CH₂)₄— | H | CH₃ | |
| 277 | 4-CH₃—C₆H₄—O— | —(CH₂)₄— | H | CH₃ | |
| 278 | C₆H₅—O— | —CH₂—CH₂—CH(CH₃)—CH₂— | H | CH₃ | |
| 279 | C₆H₅—O— | —(CH₂)₅— | H | CH₃ | |
| 280 | 3-Cl—C₆H₄—O— | —(CH₂)₅— | H | CH₃ | |
| 281 | C₆H₅—O— | —(CH₂)₃—CH(CH₃)—CH₂— | H | CH₃ | |
| 282 | C₆H₅—O— | —(CH₂)₆— | H | CH₃ | |
| 283 | 3-Cl—C₆H₅—O— | —(CH₂)₆— | H | CH₃ | |
| 284 | C₆H₅—O— | —(CH₂)₄—CH(CH₃)—CH₂— | H | CH₃ | |
| 285 | A (1*) | — | H | CH₃ | |
| 286 | A (2*) | — | H | CH₃ | oil 2950, 1720, 1434, |

TABLE 1-continued $$R^3-(X)_n-\overset{O}{\underset{\|}{C}}-O-CH_2-\underset{\underset{R^2-CH_2}{\bigg|}}{\text{C}_6H_4}-\underset{CH}{\overset{}{=}}C-COOR^1$$
(I)

| No. | R³ | (X)ₙ | R² | R¹ | mp (°C.) IR (cm⁻¹) |
|---|---|---|---|---|---|
| | | | | | 1255, 1169, 761 |
| 287 | A (3*) | — | H | CH₃ | |
| 288 | A (4*) | — | H | CH₃ | |
| 289 | A (5*) | — | H | CH₃ | |
| 290 | A (6*) | — | H | CH₃ | |
| 291 | A (7*) | — | H | CH₃ | |
| 292 | A (8*) | — | H | CH₃ | |
| 293 | A (9*) | — | H | CH₃ | |
| 294 | A (10*) | — | H | CH₃ | |
| 295 | A (11*) | — | H | CH₃ | |
| 296 | A (12*) | — | H | CH₃ | |
| 297 | A (13*) | — | H | CH₃ | |
| 298 | A (14*) | — | H | CH₃ | |
| 299 | A (15*) | — | H | CH₃ | |
| 300 | A (15*) | — | H | CH₃ | |
| 301 | A (17*) | — | H | CH₃ | |
| 302 | N-pyrrolyl | —CH(iso-C₃H₇)— | H | CH₃ | |
| 303 | 4-tert.-butyl-C₆H₄ | —CH₂—C(CH₃)=CH—CH=CH— | H | CH₃ | |
| 304 | H | —CH₂—CH(CH₃)—CH₂—CH(CH₃)— | H | CH₃ | |
| 305 | H | —CH₂—CH(CH₃)—CH₂—CH(C₂H₅)— | H | CH₃ | |
| 306 | H | —CH₂—CH(CH₃)—CH₂—CH(n-C₃H₇)— | H | CH₃ | |
| 307 | H | —CH₂—CH(CH₃)—CH₂—CH(i-C₃H₇)— | H | CH₃ | |
| 308 | H | —CH₂—C(CH₃)₂—CH₂—CH(CH₃)—CH₂— | H | CH₃ | |
| 309 | H | —(CH₂)₅—CH(C₂H₅)— | H | CH₃ | |
| 310 | H | —(CH₂)₅—CH(n-C₃H₇)— | H | CH₃ | |
| 311 | H | —(CH₂)₄—O—CH₂—C(CH₃)₂— | | | |
| 312 | H | —CH₂—O—CH₂—C(CH₃)₂— | H | CH₃ | |
| 313 | C₆H₅ | —CH=CH—(CH₂)₄— | H | CH₃ | |
| 314 | H | —CH₂—C(CH₃)₂—CH₂—CH(CH₃)₂—CH₂— | H | CH₃ | |
| 315 | H | —CH₂—CH(CH₃)—(CH₂)₂—CH(i-C₃H₇)— | H | CH₃ | |
| 316 | 1-methylcyclopropyl | — | H | CH₃ | oil 2955, 1720, 1322, 1255, 1156, 1038, 758 |
| 317 | 2-methylcyclopropyl | — | H | CH₃ | |
| 318 | 2-phenylcyclopropyl | — | H | CH₃ | |
| 319 | 1-methylcyclohexyl | — | H | CH₃ | |
| 320 | 2-Cl—C₆H₄ | —CHCl— | H | CH₃ | |
| 321 | 1-methylcyclopropyl | — | H | C₂H₅ | |
| 322 | 1-methylcyclopropyl | — | H | i-C₃H₇ | |
| 323 | 1-methylcyclopropyl | — | C₂H₅ | CH₃ | |
| 324 | 1-methylcyclopropyl | — | C₃H₇ | CH₃ | |
| 325 | 1-methylcyclopropyl | — | C₄H₉ | CH₃ | |
| 326 | 1-methylcyclopropyl | — | OCH₃ | CH₃ | |
| 327 | 1-methylcyclopropyl | — | OC₂H₅ | CH₃ | |
| 328 | 1-methylcyclopropyl | — | O-i-C₃H₇ | CH₃ | |
| 329 | 1-methylcyclopropyl | — | OC₄H₉ | CH₃ | |
| 330 | H | —(CH₂)₄—CH(CH₃)—CH₂— | OCH₃ | CH₃ | |
| 331 | H | —C(CH₃)₂— | OCH₃ | CH₃ | |
| 332 | C₆H₅ | — | OCH₃ | CH₃ | |
| 333 | C₆H₅ | —CH(CH₃)— | OCH₃ | CH₃ | |
| 334 | 1-methylcyclohexyl | — | OCH₃ | CH₃ | |
| 335 | 1-ethylcyclohexyl | — | H | CH₃ | |
| 336 | H | —CH₂— | CH₃ | CH₃ | |
| 337 | H | —CH₂—CH₂— | CH₃ | CH₃ | |
| 338 | H | —CH₂—CH(CH₃)— | CH₃ | CH₃ | |
| 339 | H | —CH₂—C(CH₃)₂— | CH₃ | CH₃ | oil 1722, 1281, 1243, 1176 |
| 340 | H | —CH=CH— | CH₃ | CH₃ | |
| 341 | H | —CH=C(CH₃)— | CH₃ | CH₃ | |
| 342 | H | —C≡C— | CH₃ | CH₃ | |
| 343 | H | —CH₂—CH₂—CH₂— | CH₃ | CH₃ | |
| 344 | H | —CH₂—CH₂—CH(CH₃)— | CH₃ | CH₃ | |
| 345 | H | —CH₂—CH(CH₃)—CH₂— | CH₃ | CH₃ | |
| 346 | H | —CH₂—CH₂—C(CH₃)₂— | CH₃ | CH₃ | |
| 347 | H | —CH₂—C(CH₃)₂—CH₂— | CH₃ | CH₃ | |
| 348 | H | —CH₂—CH₂—C(C₂H₅)₂ | CH₃ | CH₃ | |
| 349 | H | —CH=CH—CH₂— | CH₃ | CH₃ | |
| 350 | H | —CH₂—CH=CH— | CH₃ | CH₃ | |
| 351 | H | —CH₂—C(CH₃)=CH— | CH₃ | CH₃ | |
| 352 | H | —CH₂—CH=C(CH₃)— | CH₃ | CH₃ | |
| 353 | H | —(CH₂)₄— | CH₃ | CH₃ | |
| 354 | H | —CH₂—CH₂—CH₂—CH(CH₃)— | CH₃ | CH₃ | |
| 355 | H | —CH₂—CH(CH₃)—CH₂—CH₂— | CH₃ | CH₃ | |

TABLE 1-continued

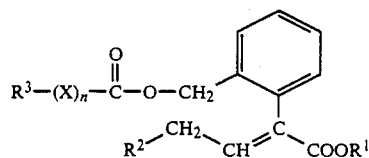

(I)

| No. | R³ | (X)ₙ | R² | R¹ | mp (°C.) IR (cm⁻¹) |
|---|---|---|---|---|---|
| 356 | H | —(CH₂)₃—C(CH₃)₂— | CH₃ | CH₃ | |
| 357 | H | —(CH₂)₃—CH(C₂H₅)— | CH₃ | CH₃ | |
| 358 | H | —(CH₂)₃—CH(n-C₃H₇)— | CH₃ | CH₃ | |
| 359 | H | —CH₂—CH=CH—CH₂— | CH₃ | CH₃ | |
| 360 | H | —CH₂—CH(CH₃)=CH—CH₂— | CH₃ | CH₃ | |
| 361 | H | —(CH₂)₅— | CH₃ | CH₃ | |
| 362 | H | —(CH₂)₄—CH(CH₃)— | CH₃ | CH₃ | |
| 363 | H | —(CH₂)₄—CH(C₂H₅)— | CH₃ | CH₃ | |
| 364 | H | —(CH₂)₃—CH(CH₃)—CH₂— | CH₃ | CH₃ | |
| 365 | H | —CH₂—CH=CH—CH=CH— | CH₃ | CH₃ | |
| 366 | H | —CH₂—C(CH₃)=CH—CH=CH— | CH₃ | CH₃ | |
| 367 | H | —(CH₂)₆— | CH₃ | CH₃ | |
| 368 | H | —(CH₂)₅—CH(CH₃)— | CH₃ | CH₃ | |
| 369 | H | —(CH₂)₄—CH(CH₃)—CH₂— | CH₃ | CH₃ | |
| 370 | H | —(CH₂)₅—CH(n-C₃H₇)— | CH₃ | CH₃ | |
| 371 | H | —(CH₂)₇— | CH₃ | CH₃ | |
| 372 | H | —(CH₂)₆—CH(CH₃)— | CH₃ | CH₃ | |
| 373 | H | —(CH₂)₅—CH(CH₃)—CH₂— | CH₃ | CH₃ | |
| 374 | H | —(CH₂)₆—C(CH₃)₂— | CH₃ | CH₃ | |
| 375 | H | —(CH₂)₈— | CH₃ | CH₃ | |
| 376 | H | —(CH₂)₉— | CH₃ | CH₃ | |
| 377 | H | —(CH₂)₁₀— | CH₃ | CH₃ | |
| 378 | H | —CHCl— | CH₃ | CH₃ | |
| 379 | H | —CCl₂— | CH₃ | CH₃ | |
| 380 | Cl | —CCl₂— | CH₃ | CH₃ | |
| 381 | H | —CHBr— | CH₃ | CH₃ | |
| 382 | H | —CBr₂— | CH₃ | CH₃ | |
| 383 | Br | —CBr₂— | CH₃ | CH₃ | |
| 384 | H | —CHF— | CH₃ | CH₃ | |
| 385 | H | —CF₂— | CH₃ | CH₃ | |
| 386 | F | —CF₂— | CH₃ | CH₃ | |
| 387 | H | —CH=CCl— | CH₃ | CH₃ | |
| 388 | H | —CCl=CCl— | CH₃ | CH₃ | |
| 389 | Cl | —C(CH₃)₂— | CH₃ | CH₃ | |
| 390 | H | —C(CH₃)₂— | CH₃ | CH₃ | |
| 391 | H | —CHCl—CH(CH₃)— | CH₃ | CH₃ | |
| 392 | H | —CHCl—C(CH₃)₂— | CH₃ | CH₃ | |
| 393 | H | —CHBr—CH(CH₃)— | CH₃ | CH₃ | |
| 394 | Br | —C(C₂H₅)₂— | CH₃ | CH₃ | |
| 395 | H | —CH(OH)— | CH₃ | CH₃ | |
| 396 | H | —CH₂—CH(OH)— | CH₃ | CH₃ | |
| 397 | H | —CH₂—CH₂—CH(OH)— | CH₃ | CH₃ | |
| 398 | H | —CH₂—CH(OH)—CH₂— | CH₃ | CH₃ | |
| 399 | H | —CH(OH)—CH₂— | CH₃ | CH₃ | |
| 400 | H | —CH(OH)—C(CH₃)₂— | CH₃ | CH₃ | |
| 401 | H | —CH₂—C(OH)(CH₃)— | CH₃ | CH₃ | |
| 402 | H | —CH₂—CH(CH₃)—CH(OH)— | CH₃ | CH₃ | |
| 403 | H | —CH=CH—CH(OH)— | CH₃ | CH₃ | |
| 404 | H | —CH=CH—CH₂—CH(OH)— | CH₃ | CH₃ | |
| 405 | CN | —CH₂— | CH₃ | CH₃ | |
| 406 | cyclopropyl | — | CH₃ | CH₃ | oil 1720, 1398, 1244, 1169 |
| 407 | cyclobutyl | — | CH₃ | CH₃ | |
| 408 | cyclopentyl | — | CH₃ | CH₃ | |
| 409 | cyclohexyl | — | CH₃ | CH₃ | |
| 410 | adamantyl | — | CH₃ | CH₃ | |
| 411 | 9-fluorenyl | — | CH₃ | CH₃ | |
| 412 | cyclopentyl | —CH₂— | CH₃ | CH₃ | |
| 413 | 3-cyclopentenyl | —CH₂— | CH₃ | CH₃ | |
| 414 | cyclohexyl | —CH₂— | CH₃ | CH₃ | |
| 415 | cyclopentyl | —CH₂—CH₂— | CH₃ | CH₃ | |
| 416 | cyclohexyl | —CH₂—CH₂— | CH₃ | CH₃ | |
| 417 | cyclohexyl | —(CH₂)₃— | CH₃ | CH₃ | |
| 418 | C₆H₅ (= phenyl) | — | CH₃ | CH₃ | |
| 419 | 2-CH₃—C₆H₄ | — | CH₃ | CH₃ | |
| 420 | 3-CH₃—C₆H₄ | — | CH₃ | CH₃ | |
| 421 | 4-CH₃—C₆H₄ | — | CH₃ | CH₃ | |
| 422 | 2,3-(CH₃)₂—C₆H₃ | — | CH₃ | CH₃ | |
| 423 | 2,4-(CH₃)₂—C₆H₃ | — | CH₃ | CH₃ | |
| 424 | 2,6-(CH₃)₂—C₆H₃ | — | CH₃ | CH₃ | |
| 425 | 3,4-(CH₃)₂—C₆H₃ | — | CH₃ | CH₃ | |
| 426 | 3,5-(CH₃)₂—C₆H₃ | — | CH₃ | CH₃ | |

TABLE 1-continued

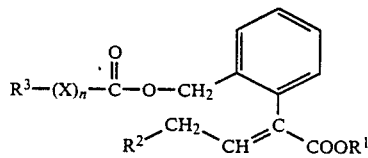

(I)

| No. | R³ | (X)ₙ | R² | R¹ | mp (°C.) IR (cm⁻¹) |
|---|---|---|---|---|---|
| 427 | 2,4,6-(CH₃)₂—C₆H₂ | — | CH₃ | CH₃ | |
| 428 | 4-t-C₄H₉—C₆H₄ | — | CH₃ | CH₃ | |
| 429 | 2-C₆H₅—C₆H₄ | — | CH₃ | CH₃ | |
| 430 | 4-C₆H₅—C₆H₄ | — | CH₃ | CH₃ | |
| 431 | 2-benzyl-C₆H₄ | — | CH₃ | CH₃ | |
| 432 | 4-benzyl-C₆H₄ | — | CH₃ | CH₃ | |
| 433 | 2-Cl-C₆H₄ | — | CH₃ | CH₃ | |
| 434 | 3-Cl—C₆H₄ | — | CH₃ | CH₃ | |
| 435 | 4-Cl—C₆H₄ | — | CH₃ | CH₃ | |
| 436 | 2,4-Cl₂—C₆H₃ | — | CH₃ | CH₃ | |
| 437 | 2,5-Cl₂—C₆H₃ | — | CH₃ | CH₃ | |
| 438 | 2,6-Cl₂—C₆H₃ | — | CH₃ | CH₃ | |
| 439 | 3,4-Cl₂—C₆H₃ | — | CH₃ | CH₃ | |
| 440 | 3,5-Cl₂—C₆H₃ | — | CH₃ | CH₃ | |
| 441 | 2,4,5-Cl3—C₆H₂ | — | CH₃ | CH₃ | |
| 442 | 2,3,4,5,6-Cl₅—C₆ | — | CH₃ | CH₃ | |
| 443 | 2-F,4-Cl—C₆H₃ | — | CH₃ | CH₃ | |
| 444 | 2-F—C₆H₄ | — | CH₃ | CH₃ | |
| 445 | 3-F—C₆H₄ | — | CH₃ | CH₃ | |
| 446 | 4-F—C₆H₄ | — | CH₃ | CH₃ | |
| 447 | 2,4-F₂—C₆H₃ | — | CH₃ | CH₃ | |
| 448 | 2,6-F₂—C₆H₃ | — | CH₃ | CH₃ | |
| 449 | 2,3,4,5,6-F₅—C₆ | — | CH₃ | CH₃ | |
| 450 | 2-CF₃—C₆H₄ | — | CH₃ | CH₃ | |
| 451 | 3-CF₃—C₆H₄ | — | CH₃ | CH₃ | |
| 452 | 4-CF₃—C₆H₄ | — | CH₃ | CH₃ | |
| 453 | 2-OCH₃—C₆H₄ | — | CH₃ | CH₃ | |
| 454 | 3-OCH₃—C₆H₄ | — | CH₃ | CH₃ | |
| 455 | 4-OCH₃—C₆H₄ | — | CH₃ | CH₃ | |
| 456 | 2-phenoxy-C₆H₄ | — | CH₃ | CH₃ | |
| 457 | 3-phenoxy-C₆H₄ | — | CH₃ | CH₃ | |
| 458 | 4-phenoxy-C₆H₄ | — | CH₃ | CH₃ | |
| 459 | 4-ethoxy-C₆H₄ | — | CH₃ | CH₃ | |
| 460 | 2-phenoxyethoxy—C₆H₄ | — | CH₃ | CH₃ | |
| 461 | 2-(2'-Cl—phenoxyethoxy)-C₆H₄ | — | CH₃ | CH₃ | |
| 462 | 2-(3'-Cl-phenoxyethoxy)-C₆H₄ | — | CH₃ | CH₃ | |
| 463 | 2-(4'-Cl-phenoxyethoxy)-C₆H₄ | — | CH₃ | CH₃ | |
| 464 | 3-phenoxyethoxy-C₆H₄ | — | CH₃ | CH₃ | |
| 465 | 3-(4'-Cl-phenoxyethoxy)-C₆H₄ | — | CH₃ | CH₃ | |
| 466 | 4-phenoxyethoxy-C₆H₄ | — | CH₃ | CH₃ | |
| 467 | 2-phenoxypropoxy-C₆H₄ | — | CH₃ | CH₃ | |
| 468 | 3-phenoxypropoxy-C₆H₄ | — | CH₃ | CH₃ | |
| 469 | 4-phenoxypropoxy-C₆H₄ | — | CH₃ | CH₃ | |
| 470 | C₆H₅ | —CH₂— | CH₃ | CH₃ | |
| 471 | 2-CH₃—C₆H₄ | —CH₂— | CH₃ | CH₃ | |
| 472 | C₆H₅ | —CH(CH₃)— | CH₃ | CH₃ | |
| 473 | 4-phenyl-C₆H₄ | —CH₂— | CH₃ | CH₃ | |
| 474 | 2-F—C₆H₄ | —CH₂— | CH₃ | CH₃ | |
| 475 | 3-F—C₆H₄ | —CH₂— | CH₃ | CH₃ | |
| 476 | 4-F—C₆H₄ | —CH₂— | CH₃ | CH₃ | |
| 477 | 2-Cl—C₆H₄ | —CH₂— | CH₃ | CH₃ | |
| 478 | 3-Cl—C₆H₄ | —CH₂— | CH₃ | CH₃ | |
| 479 | 4-Cl—C₆H₄ | —CH₂— | CH₃ | CH₃ | |
| 480 | 2,4-Cl₂—C₆H₃ | —CH₂— | CH₃ | CH₃ | |
| 481 | 2,6-Cl₂—C₆H₃ | —CH₂— | CH₃ | CH₃ | |
| 482 | 2-Cl,4-F—C₆H₃ | —CH₂— | CH₃ | CH₃ | |
| 483 | 2-ethoxy-C₆H₄ | —CH₂— | CH₃ | CH₃ | |
| 484 | 4-ethoxy-C₆H₄ | —CH₂— | CH₃ | CH₃ | |
| 485 | 2-OCH₃—C₆H₄ | —CH₂— | CH₃ | CH₃ | |
| 486 | 4-OCH₃—C₆H₄ | —CH₂— | CH₃ | CH₃ | |
| 487 | 4-t-C₄H₉—C₆H₄ | —CH₂— | CH₃ | CH₃ | |
| 488 | C₆H₅ | —CH(iso-C₃H₇)— | CH₃ | CH₃ | |
| 489 | 4-Cl—C₆H₄ | —CH(iso-C₃H₇)— | CH₃ | CH₃ | |
| 490 | 4-F—C₆H₄ | —CH(iso-C₃H₇)— | CH₃ | CH₃ | |
| 491 | 4-OCF₂H—C₆H₄ | —CH(iso-C₃H₇)— | CH₃ | CH₃ | |
| 492 | C₆H₅ | —CH(OH)— | CH₃ | CH₃ | |
| 493 | 2-OCH₃—C₆H₄ | —CH(OH)— | CH₃ | CH₃ | |
| 494 | 3-OCH₃—C₆H₄ | —CH(OH)— | CH₃ | CH₃ | |
| 495 | 4-OCH₃—C₆H₄ | —CH(OH)— | CH₃ | CH₃ | |
| 496 | 4-Cl—C₆H₄ | —CH(OH)— | CH₃ | CH₃ | |
| 497 | C₆H₅ | —CH(CH₂OH)— | CH₃ | CH₃ | |
| 498 | C₆H₅ | —CH₂—CH₂— | CH₃ | CH₃ | |

TABLE 1-continued

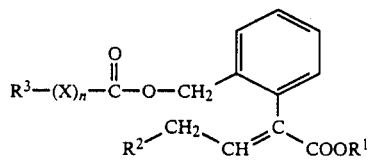

(I)

| No. | R³ | (X)ₙ | R² | R¹ | mp (°C.) IR (cm⁻¹) |
|---|---|---|---|---|---|
| 499 | C₆H₅ | —CH(CH₃)—CH₂— | CH₃ | CH₃ | |
| 500 | C₆H₅ | —CH₂—CH(CH₃)— | CH₃ | CH₃ | |
| 501 | C₆H₅ | —CH(CH₃)—CH(CH₃)— | CH₃ | CH₃ | |
| 502 | C₆H₅ | —CH(C₆H₅)—CH₂— | CH₃ | CH₃ | |
| 503 | 4-t-C₄H₉—C₆H₄ | —CH₂—CH₂— | CH₃ | CH₃ | |
| 504 | 4-t-C₄H₉—C₆H₄ | —CH₂—CH(CH₃)— | CH₃ | CH₃ | |
| 505 | 2-Cl—C₆H₄ | —CH₂—CH₂— | CH₃ | CH₃ | |
| 506 | 3-Cl—C₆H₄ | —CH₂—CH₂— | CH₃ | CH₃ | |
| 507 | 4-Cl—C₆H₄ | —CH₂—CH₂— | CH₃ | CH₃ | |
| 508 | 2-F—C₆H₄ | —CH₂—CH₂— | CH₃ | CH₃ | |
| 509 | 3-F—C₆H₄ | —CH₂—CH₂— | CH₃ | CH₃ | |
| 510 | 4-F—C₆H₄ | —CH₂—CH₂— | CH₃ | CH₃ | |
| 511 | 2-OCH₃—C₆H₄ | —CH₂—CH₂— | CH₃ | CH₃ | |
| 512 | 4-OCH₃—C₆H₄ | —CH₂—CH₂— | CH₃ | CH₃ | |
| 513 | C₆H₅ | —CH=CH— | CH₃ | CH₃ | oil 1716, 1637, 1244, 1164, 767 |
| 514 | 2-Cl—C₆H₄ | —CH=CH— | CH₃ | CH₃ | |
| 515 | 3-Cl—C₆H₄ | —CH=CH— | CH₃ | CH₃ | |
| 516 | 4-Cl—C₆H₄ | —CH=CH— | CH₃ | CH₃ | |
| 517 | 2,6-Cl₂—C₆H₃ | —CH=CH— | CH₃ | CH₃ | |
| 518 | 2,4-Cl₂—C₆H₃ | —CH=CH— | CH₃ | CH₃ | |
| 519 | 2-F—C₆H₄ | —CH=CH— | CH₃ | CH₃ | |
| 520 | 3-F—C₆H₄ | —CH=CH— | CH₃ | CH₃ | |
| 521 | 4-F—C₆H₄ | —CH=CH— | CH₃ | CH₃ | |
| 522 | 2-CF₃—C₆H₄ | —CH=CH— | CH₃ | CH₃ | |
| 523 | 4-CF₃—C₆H₄ | —CH=CH— | CH₃ | CH₃ | |
| 524 | 2-CH₃—C₆H₄ | —CH=CH— | CH₃ | CH₃ | |
| 525 | 4-CH₃—C₆H₄ | —CH=CH— | CH₃ | CH₃ | |
| 526 | 4-i-C₃H₇—C₆H₄ | —CH=CH— | CH₃ | CH₃ | |
| 527 | 4-t-C₄H₉—C₆H₄ | —CH=CH— | CH₃ | CH₃ | |
| 528 | 2-OCH₃—C₆H₄ | —CH=CH— | CH₃ | CH₃ | |
| 529 | 3-OCH₃—C₆H₄ | —CH=CH— | CH₃ | CH₃ | |
| 530 | 4-OCH₃—C₆H₄ | —CH=CH— | CH₃ | CH₃ | |
| 351 | 2-phenoxy-C₆H₄ | —CH=CH— | CH₃ | CH₃ | |
| 532 | 3-phenoxy-C₆H₄ | —CH=CH— | CH₃ | CH₃ | |
| 533 | 4-phenoxy-C₆H₄ | —CH=CH— | CH₃ | CH₃ | |
| 534 | C₆H₅ | —(CH₂)₃— | CH₃ | CH₃ | |
| 535 | C₆H₅ | —CH(CH₃)—CH₂—CH₂— | CH₃ | CH₃ | |
| 536 | C₆H₅ | —CH₂—CH(CH₃)—CH₂— | CH₃ | CH₃ | |
| 537 | C₆H₅ | —CH₂—CH₂—CH(CH₃)— | CH₃ | CH₃ | |
| 538 | 2-Cl—C₆H₄ | —(CH₂)₃— | CH₃ | CH₃ | |
| 539 | 4-Cl—C₆H₄ | —(CH₂)₃— | CH₃ | CH₃ | |
| 540 | 2-OCH₃—C₆H₄ | —(CH₂)₃— | CH₃ | CH₃ | |
| 541 | 4-OCH₃—C₆H₄ | —(CH₂)₃— | CH₃ | CH₃ | |
| 542 | 4-t-C₄H₉—C₆H₄ | —(CH₂)₃— | CH₃ | CH₃ | |
| 543 | C₆H₅ | —CH=CH—CH₂— | CH₃ | CH₃ | |
| 544 | C₆H₅ | —(CH₂)₄— | CH₃ | CH₃ | |
| 545 | 2-Cl—C₆H₄ | —(CH₂)₄— | CH₃ | CH₃ | |
| 546 | 4-Cl—C₆H₄ | —(CH₂)₄— | CH₃ | CH₃ | |
| 547 | 2-OCH₃—C₆H₄ | —(CH₂)₄— | CH₃ | CH₃ | |
| 548 | 4-OCH₃—C₆H₄ | —(CH₂)₄— | CH₃ | CH₃ | |
| 549 | 4-CF₃—C₆H₄ | —(CH₂)₄— | CH₃ | CH₃ | |
| 550 | 2-CH₃—C₆H₄ | —(CH₂)₄— | CH₃ | CH₃ | |
| 551 | 4-CH₃—C₆H₄ | —(CH₂)₄— | CH₃ | CH₃ | |
| 552 | C₆H₅ | —CH₂—CH₂—CH(CH₃)—CH₂— | CH₃ | CH₃ | |
| 553 | C₆H₅ | —(CH₂)₅— | CH₃ | CH₃ | |
| 554 | 2-CH₃—C₆H₄ | —(CH₂)₅— | CH₃ | CH₃ | |
| 555 | 4-CH₃—C₆H₄ | —(CH₂)₅— | CH₃ | CH₃ | |
| 556 | 2-Cl—C₆H₄ | —(CH₂)₅— | CH₃ | CH₃ | |
| 557 | 4-Cl—C₆H₄ | —(CH₂)₅— | CH₃ | CH₃ | |
| 558 | 2-OCH₃—C₆H₄ | —(CH₂)₅— | CH₃ | CH₃ | |
| 559 | 4-OCH₃—C₆H₄ | —(CH₂)₅— | CH₃ | CH₃ | |
| 560 | 4-CF₃—C₆H₄ | —(CH₂)₅— | CH₃ | CH₃ | |
| 561 | C₆H₅ | —CH₂—CH₂—CH₂—CH(CH₃)—CH₂— | CH₃ | CH₃ | |
| 562 | C₆H₅ | —CH₂—CH(CH₃)—CH₂—CH(CH₃)—CH₂ | CH₃ | CH₃ | |
| 563 | 4-t-C₄H₉—C₆H₄ | —CH₂—CH(CH₃)—CH₂—CH(CH₃)—CH₂— | CH₃ | CH₃ | |
| 564 | C₆H₅ | —(CH₂)₆— | CH₃ | CH₃ | |
| 565 | C₆H₅ | —(CH₂)₄—CH(CH₃)—CH₂— | CH₃ | CH₃ | |
| 566 | C₆H₅—O— | —CH₂— | CH₃ | CH₃ | |
| 567 | 2-Cl—C₆H₄—O— | —CH₂— | CH₃ | CH₃ | |
| 568 | 3-Cl—C₆H₄—O— | —CH₂— | CH₃ | CH₃ | |
| 569 | 4-Cl—C₆H₄—O— | —CH₂— | CH₃ | CH₃ | |

TABLE 1-continued $$R^3-(X)_n-\overset{O}{\underset{}{C}}-O-CH_2 \text{-[2-substituted phenyl with }=C(COOR^1)-CH=CH-CH_2-R^2\text{ substituent]}$$ (I)

| No. | R³ | (X)ₙ | R² | R¹ | mp (°C.) IR (cm⁻¹) |
|---|---|---|---|---|---|
| 570 | 2,4-Cl₂—C₆H₃—O— | —CH₂— | CH₃ | CH₃ | |
| 571 | 2-CH₃—C₆H₄—O— | —CH₂— | CH₃ | CH₃ | |
| 572 | 4-CH₃—C₆H₄—O— | —CH₂— | CH₃ | CH₃ | |
| 573 | 2-OCH₃—C₆H₄—O— | —CH₂— | CH₃ | CH₃ | |
| 574 | 4-OCH₃—C₆H₄—O— | —CH₂— | CH₃ | CH₃ | |
| 575 | 4-CF₃—C₆H₄—O— | —CH₂— | CH₃ | CH₃ | |
| 576 | C₆H₅—O— | —CH(CH₃)— | CH₃ | CH₃ | |
| 577 | C₆H₅—O— | —CH₂—CH₂— | CH₃ | CH₃ | |
| 578 | 2-Cl—C₆H₄—O— | —CH₂—CH₂— | CH₃ | CH₃ | |
| 579 | 4-Cl—C₆H₄—O— | —CH₂—CH₂— | CH₃ | CH₃ | |
| 580 | 2-CH₃—C₆H₄—O— | —CH₂—CH₂— | CH₃ | CH₃ | |
| 581 | 4-CH₃—C₆H₄—O— | —CH₂—CH₂— | CH₃ | CH₃ | |
| 582 | 2-OCH₃—C₆H₄—O— | —CH₂—CH₂— | CH₃ | CH₃ | |
| 583 | 4-OCH₃—C₆H₄—O— | —CH₂—CH₂— | CH₃ | CH₃ | |
| 584 | 4-t-C₄H₉—C₆H₄—O— | —CH₂—CH₂— | CH₃ | CH₃ | |
| 585 | 4-sec.-C₄H₉—C₆H₄—O— | —CH₂—CH₂— | CH₃ | CH₃ | |
| 586 | C₆H₅—O— | —(CH₂)₃— | CH₃ | CH₃ | |
| 587 | 2-Cl—C₆H₄—O— | —(CH₂)₃— | CH₃ | CH₃ | |
| 588 | 4-Cl—C₆H₄—O— | —(CH₂)₃— | CH₃ | CH₃ | |
| 589 | 3-F—C₆H₄—O— | —(CH₂)₃— | CH₃ | CH₃ | |
| 590 | 4-F—C₆H₄—O— | —(CH₂)₃— | CH₃ | CH₃ | |
| 591 | 2-CH₃—C₆H₄—O— | —(CH₂)₃— | CH₃ | CH₃ | |
| 592 | 4-CH₃—C₆H₄—O— | —(CH₂)₃— | CH₃ | CH₃ | |
| 593 | 2-OCH₃—C₆H₄—O— | —(CH₂)₃— | CH₃ | CH₃ | |
| 594 | 4-OCH₃—C₆H₄—O— | —(CH₂)₃— | CH₃ | CH₃ | |
| 595 | 2,4-Cl₂—C₆H₃—O— | —(CH₂)₃— | CH₃ | CH₃ | |
| 596 | 4-Cl—C₆H₄—O— | —CH(CH₃)—CH₂—CH₂— | CH₃ | CH₃ | |
| 597 | 2-CF₃—C₆H₄—O— | —(CH₂)₃— | CH₃ | CH₃ | |
| 598 | 3-CF₃—C₆H₄—O— | —(CH₂)₃— | CH₃ | CH₃ | |
| 599 | 4-CF₃—C₆H₄—O— | —(CH₂)₃— | CH₃ | CH₃ | |
| 600 | 4-t-butoxy-C₆H₄—O— | —(CH₂)₃— | CH₃ | CH₃ | |
| 601 | 2-CH₃,4-Cl—C₆H₃—O— | —(CH₂)₃— | CH₃. | CH₃ | |
| 602 | 4-C₂H₅—C₆H₄—O— | —(CH₂)₃— | CH₃ | CH₃ | |
| 603 | 4-iso-C₃H₇—C₆H₄—O— | —(CH₂)₃— | CH₃ | CH₃ | |
| 604 | 4-t-C₄H₉—C₆H₄—O— | —(CH₂)₃— | CH₃ | CH₃ | |
| 605 | C₆H₅—O— | —CH₂—CH(CH₃)—CH₂— | CH₃ | CH₃ | |
| 606 | C₆H₅—O— | —(CH₂)₄— | CH₃ | CH₃ | |
| 607 | 2-Cl—C₆H₄—O— | —(CH₂)₄— | CH₃ | CH₃ | |
| 608 | 4-Cl—C₆H₄—O— | —(CH₂)₄— | CH₃ | CH₃ | |
| 609 | 2,4-Cl₂—C₆H₃—O— | —(CH₂)₄— | CH₃ | CH₃ | |
| 610 | 2,6-Cl₂—C₆H₃—O— | —(CH₂)₄— | CH₃ | CH₃ | |
| 611 | 2-CH₃—C₆H₄—O— | —(CH₂)₄— | CH₃ | CH₃ | |
| 612 | 4-CH₃—C₆H₄—O— | —(CH₂)₄— | CH₃ | CH₃ | |
| 613 | C₆H₅—O— | —CH₂—CH₂—CH(CH₃)—CH₂— | CH₃ | CH₃ | |
| 614 | C₆H₅—O— | —(CH₂)₅— | CH₃ | CH₃ | |
| 615 | 3-Cl—C₆H₄—O— | —(CH₂)₅— | CH₃ | CH₃ | |
| 616 | C₆H₅—O— | —(CH₂)₃—CH(CH₃)—CH₂— | CH₃ | CH₃ | |
| 617 | C₆H₅—O— | —(CH₂)₆— | CH₃ | CH₃ | |
| 618 | 3-Cl—C₆H₅—O— | —(CH₂)₆— | CH₃ | CH₃ | |
| 619 | C₆H₅—O— | —(CH₂)₄—CH(CH₃)—CH₂— | CH₃ | CH₃ | |
| 620 | A (1*) | — | CH₃ | CH₃ | oil 2955, 1721, 1434, 1243, 1176, 755 |
| 622 | A (3*) | — | CH₃ | CH₃ | |
| 623 | A (4*) | — | CH₃ | CH₃ | |
| 624 | A (5*) | — | CH₃ | CH₃ | |
| 625 | A (6*) | — | CH₃ | CH₃ | |
| 626 | A (7*) | — | CH₃ | CH₃ | |
| 627 | A (8*) | — | CH₃ | CH₃ | |
| 628 | A (9*) | — | CH₃ | CH₃ | |
| 629 | A (10*) | — | CH₃ | CH₃ | |
| 630 | A (11*) | — | CH₃ | CH₃ | |
| 631 | A (12*) | — | CH₃ | CH₃ | |
| 632 | A (13*) | — | CH₃ | CH₃ | |
| 633 | A (14*) | — | CH₃ | CH₃ | |
| 634 | A (15*) | — | CH₃ | CH₃ | |
| 635 | A (15*) | — | CH₃ | CH₃ | |
| 636 | A (17*) | — | CH₃ | CH₃ | |
| 637 | N-pyrrolyl | —CH(iso-C₃H₇)— | CH₃ | CH₃ | |
| 638 | 4-tert.-butyl-C₆H₄ | —CH₂—C(CH₃)=CH—CH=CH— | CH₃ | CH₃ | |
| 639 | H | —CH₂—CH(CH₃)—CH₂—CH(CH₃)— | CH₃ | CH₃ | |
| 640 | H | —CH₂—CH(CH₃)—CH₂—CH(C₂H₅)— | CH₃ | CH₃ | |
| 641 | H | —CH₂—CH(CH₃)—CH₂—CH(n-C₃H₇)— | CH₃ | CH₃ | |

TABLE 1-continued $$R^3-(X)_n-\overset{\overset{O}{\|}}{C}-O-CH_2-\underset{\underset{R^2}{CH_2}}{\overset{}{\bigcirc}}\underset{CH}{\diagdown}\overset{C}{\diagup}\overset{}{\diagdown}COOR^1 \tag{I}$$

| No. | $R^3$ | $(X)_n$ | $R^2$ | $R^1$ | mp (°C.) IR (cm$^{-1}$) |
|---|---|---|---|---|---|
| 642 | H | —CH$_2$—CH(CH$_3$)—CH$_2$—CH(i-C$_3$H$_7$)— | CH$_3$ | CH$_3$ | |
| 643 | H | —CH$_2$—C(CH$_3$)$_2$—CH$_2$—CH(CH$_3$)—CH$_2$— | CH$_3$ | CH$_3$ | |
| 644 | H | —(CH$_2$)$_5$—CH(C$_2$H$_5$)— | CH$_3$ | CH$_3$ | |
| 645 | H | —(CH$_2$)$_5$—CH(n-C$_3$H$_7$)— | CH$_3$ | CH$_3$ | |
| 646 | H | —(CH$_2$)$_4$—O—CH$_2$—C(CH$_3$)$_2$— | CH$_3$ | CH$_3$ | |
| 647 | H | —CH$_2$—O—CH$_2$—C(CH$_3$)$_2$— | CH$_3$ | CH$_3$ | |
| 648 | C$_6$H$_5$ | —CH=CH—(CH$_2$)$_4$— | CH$_3$ | CH$_3$ | |
| 649 | H | —CH$_2$—C(CH$_3$)$_2$—CH$_2$—CH(CH$_3$)$_2$—CH$_2$— | CH$_3$ | CH$_3$ | |
| 650 | H | —CH$_2$—CH(CH$_3$)—(CH$_2$)$_2$—CH(i-C$_3$H$_7$)— | CH$_3$ | CH$_3$ | |
| 651 | 1-methylcyclopropyl | — | CH$_3$ | CH$_3$ | oil 2967, 1720, 1322, 1243, 1156, 755 |
| 652 | 2-methylcyclopropyl | — | CH$_3$ | CH$_3$ | |
| 653 | 2-phenylcyclopropyl | — | CH$_3$ | CH$_3$ | |
| 654 | 1-methylcyclohexyl | — | CH$_3$ | CH$_3$ | |
| 655 | 2-Cl—C$_6$H$_4$ | —CHCl— | CH$_3$ | CH$_3$ | |
| 656 | 1-methylcyclopropyl | — | CH$_3$ | C$_2$H$_5$ | |
| 657 | 1-methylcyclopropyl | — | CH$_3$ | i-C$_3$H$_7$ | |

In general terms the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis scab) in apples,
Helminthosporium species in cereals,
Septoria nodorum in wheat,
Botrytis cinerea gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics e.g., xylene, chlorinated aromatics e.g., chlorobenzenes, paraffins (e.g.. crude oil fractions), alcohols e.g., methanol, butanol, ketones e.g.. cyclohexanone), amines (e.g., ethanolamine, dimethylformamide), and water: carriers such as ground natural minerals (e.g., kaolins aluminas, talc and chalk and ground synthetic minerals (e.g., highly disperse silica and silicates): emulsifiers such as nonionic and anionic emulsifiers e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 286 is mixed with 10 parts by weight of N-methyl-α-pyrrolidone. A mixture is obtained which is suitable for application in the form of very fine drops.

II. 20 parts by weight of compound no. 286 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 286 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 286 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 286 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water a spray liquor is obtained.

VI. 3 parts by weight of compound no. 286 is intimately mixed with 97 parts by weight of particulate kaolin. A dust is obtained containing 3% by weight of the active ingredient.

VII. 30 parts by weight of compound no. 286 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 286 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 286 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides. insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are,
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamy) disulfide;

nitro derivatives, such as
dinitro (1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances such as
2-heptadecylimidazol-2-yl acetate,
2.4-dichloro-6-(o-chloroanilino)-s-triazine,
0,0-diethyl phthalimidophosphonothioate,
5-amino-1-[-bis-(dimethylamino)-phosphonyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N',N'-dimethyl-N-phenylsulfuric acid diamide,
5-ethoxy-3-trichloromethyl-1,2,3-thiadiazole,
2-thiocyanatomethyithiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5 dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2,-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea, 1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboxmde,
2-cyano-[N-(ethylamnocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-amnopyridine, and
1-((bis-(4-fluorophenyl)-methylsilyl)-methyl)-1H-1,2,4-triazole.

Use examples

For comparison purposes. N-tridecyl-2,6-dimethylmorpholine (A)-disclosed in DE 1,164,152—and the compound 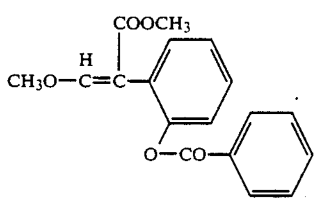 (B)

—disclosed in EP-178,826—were used.

USE EXAMPLE 1

Action on wheat brown rust

Leaves of pot-grown wheat seedlings of the "Frühgold" variety were dusted with spores of brown rust (Puccinia recondita). The pots were then placed for 24 hours at 20° to 22° C. in a high-humidity (90-95%) chamber. During this period the spores germinated and the germ tubes penetrated the leaf tissue. The infected plants were then sprayed to runoff with aqueous liquors containing dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 286 and 316, applied as 0.025 wt % spray liquors, have a better fungicidal action (90%) than the prior art active ingredients A (35%) and B (35%).

USE EXAMPLE 2

Action on Pyricularia oryzae (protective)

Leaves of pot-grown rice seedlings of the "Bahia" variety were sprayed to runoff with aqueous emulsions containing dry basis) 80% of active ingredient and 20% of emulsifier, and inoculated 24 hours later with an aqueous spore suspension of Pyricularia oryzae. The plants were subsequently placed in a climatic cabinet at 22° to 24° C. and a relative humidity of 95 to 99%. The spread of the disease was assessed after 6 days.

The results show that active ingredients 286, 83, 178 and 513, applied as 0.05% spray liquors have a better fungicidal action (97%) than prior art active ingredient A (55%).

We claim:

1. Ortho-substituted benzyl carboxylates of the formula I (I)

where $R^1$ is $C_1$–$C_5$-alkyl, $R^2$ is hydrogen, $C_1$–$C_4$-alkoxy, $R^3$ is hydrogen, halogen, cyano, aryl or aryloxy, the aromatic ring being unsubstituted or substituted by one or more of the following radicals: $C_1$–$C_6$-alkyl, $C_2$–$C_4$- alkenyl, $C_1$–$C_2$-haloalkyl, $C_1$–$C_6$-alkoxy, $C_1$–$C_4$-alkoxy-$C_1$–$C_4$-alkyl, aryl, aryl-$C_1$–$C_2$-alkyl, aryloxy, aryloxy-$C_1$–$C_4$-alkyl, aryloxy-$C_1$–$C_4$-alkoxy, haloaryloxy-$C_1$–$C_4$-alkoxy, halogen, halo-$C_1$–$C_4$-alkoxy, $C_1$–$C_4$-alkylthio, thiocyanato, cyano, nitro, or $R^3$ is heteroaryl, adamantyl, fluorenyl or $C_3$–$C_7$-cycloalkyl or $C_5$–$C_6$-cycloalkenyl, the radicals being unsubstituted or substituted by $C_1$–$C_4$-alkyl, methyl, ethyl, halogen, $C_1$–$C_2$-haloalkyl, $C_3$–$C_4$-alkenyl, $C_2$–$C_4$-haloalkenyl, methoxycarbonyl-$C_3$–$C_4$-alkenyl, cyclopentylidenemethyl, halophenyl, $C_1$–$C_2$-alkoxyphenyl or $C_1$–$C_4$-alkylphenyl, X is straight-chain or branched, saturated or unsaturated $C_1$–$C_{12}$-alkylene which is unsubstituted or substituted by halogen or hydroxyl, and n is 0 or 1.

2. A process for combating fungi, wherein the fungi or the materials, plants, seed or the soil are treated with a fungicidally effective amount of a compound of the formula I

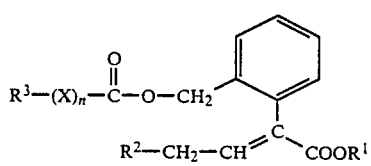

where
R$^1$ is C$_1$-C$_5$-alkyl,
R$^2$ is hydrogen, C$_1$-C$_4$-alkyl or C$_1$-C$_4$-alkoxy,
R$^3$ is hydrogen, halogen, cyano, aryl or aryloxy, the aromatic ring being unsubstituted or substituted by one or more of the following radicals:
C$_1$-C$_6$-alkyl, C$_2$-C$_4$-alkenyl, C$_1$-C$_2$-haloalkyl, C$_1$-C$_6$-alkoxy, C$_1$-C$_4$-alkoxy-C$_1$-C$_4$-alkyl, aryl, aryl-C$_1$-C$_2$-alkyl, aryloxy, aryloxy-C$_1$-C$_4$-alkyl, aryloxy-C$_1$-C$_4$-alkoxy, haloaryloxy-C$_1$-C$_4$-alkoxy, halogen, halo-C$_1$-C$_4$-alkoxy, C$_1$-C$_4$-alkylthio, thiocyanato, cyano, nitro, or R$^3$ is heteroaryl, adamantyl, fluorenyl or C$_3$-C$_7$-cycloalkyl or C$_5$-C$_6$-cycloalkenyl, the radicals being unsubstituted or substituted by C$_1$-C$_4$-alkyl, methyl, ethyl, halogen, C$_1$-C$_2$-haloalkyl, C$_3$-C$_4$-alkenyl, C$_2$-C$_4$-haloalkenyl, methoxycarbonyl-C$_3$-C$_4$-alkenyl, cyclopentylidenemethyl, halophenyl, C$_1$-C$_2$-alkoxyphenyl or C$_1$-C$_4$-alkylphenyl,
X is straight-chain or branched, saturated or unsaturated C$_1$-C$_{12}$-alkylene which is unsubstituted or substituted by halogen or hydroxyl, and
n is 0 or 1.

3. A fungicide containing an inert carrier and a fungicidally effective amount of a compound of the formula I

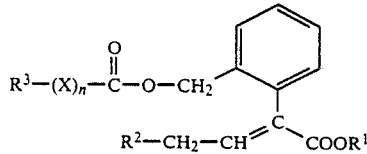

where
R$^1$ is C$_1$-C$_5$-alkyl,
R$^2$ is hydrogen, C$_1$-C$_4$-alkyl or C$_1$-C$_4$-alkoxy,
R$^3$ is hydrogen, halogen, cyano, aryl or aryloxy, the aromatic ring being unsubstituted or substituted by one or more of the following radicals:
C$_1$-C$_6$-alkyl, C$_2$-C$_4$-alkenyl, C$_1$-C$_2$-haloalkyl, C$_1$-C$_6$-alkoxy, C$_1$-C$_4$-alkoxy-C$_1$-C$_4$-alkyl, aryl, aryl-C$_1$-C$_2$-alkyl, aryloxy, aryloxy-C$_1$-C$_4$-alkyl, aryloxy-C$_1$-C$_4$-alkoxy, haloaryloxy-C$_1$-C$_4$-alkoxy, halogen, halo-C$_1$-C$_4$-alkoxy, C$_1$-C$_4$-alkylthio, thiocyanato, cyano, nitro, or R$_3$ is heteroaryl, adamantyl, fluorenyl or C$_3$-C$_7$-cycloalkyl or C$_5$-C$_6$-cycloalkenyl, the radicals being unsubstituted or substituted by C$_1$-C$_4$-alkyl, methyl, ethyl, halogen, C$_1$-C$_2$-haloalkyl, C$_3$-C$_4$-alkenyl, C$_2$-C$_4$-haloalkenyl, methoxycarbonyl-C$_3$-C$_4$-alkenyl, cyclopentylidenemethyl, halophenyl, C$_1$-C$_2$-alkoxyphenyl or C$_1$-C$_4$-alkylphenyl,
X is straight-chain or branched, saturated or unsaturated C$_1$-C$_{12}$-alkylene which is unsubstituted or substituted by halogen or hydroxyl, and
n is 0 or 1.

4. Methyl α-[ortho-(2,2-dimethyl-3(2',2'-dichlorovinyl)-cyclopropyl-carboxymethylene)-phenyl]-β-methylacrylate.

5. Methyl α-[ortho-(2,2-dimethyl-3(2',2'-dichlorovinyl-cyclopropyl-carboxymethylene)-phenyl]-β-ethylacrylate.

6. Methyl α-[ortho-(1-methylcyclopropylcarboxymethylene)-phenyl]-β-ethylacrylate.

7. An ortho-substituted benzyl carboxylate of the formula I according to claim 1, wherein R$^1$ is methyl, R$^2$ is hydrogen and R$^3$ is 1-methylcyclopropyl.

8. A process according to claim 2, wherein the compound of the formula I R$^1$ is methyl, R$^2$ is hydrogen and R$^3$ is 1-methylcyclopropyl.

9. A fungicide containing an inert carrier in a funcidial effective amount of the compound of the formula I according to claim 3, wherein in the compound of the formula I R$^1$ is methyl, R$^2$ is hydrogen and R$^3$ is 1-methylcyclopropyl.

10. An ortho-substituted benzyl carboxylate of the formula I

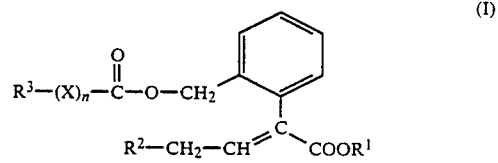

wherein
R$^1$ is C$_1$-C$_5$-alkyl,
R$^2$ is hydrogen, C$_1$-C$_4$-alkyl or C$_1$-C$_4$-alkoxy,
R$^3$ is hydrogen; halogen; C$_3$-C$_7$-cycloalkyl; C$_5$-C$_6$-cycloalkenyl; adamantyl; fluorenyl; C$_3$-C$_7$-cycloalkyl or C$_5$-C$_6$-cycloalkenyl substituted by C$_1$-C$_4$-alkyl, halogen, C$_1$-C$_2$-haloalkyl, C$_3$-C$_4$-alkenyl, C$_2$-C$_4$-haloalkenyl or cyclopentylidenemethyl,
X is a straight chain or branched saturated or unsaturated C$_1$-C$_{12}$-alkylene or a C$_1$-C$_{12}$-alkylene substituted by halogen or hydroxyl, and
n is 0 or 1.

11. The carboxylate of claim 10, wherein R$^2$ is hydrogen.

12. The carboxylate of claim 10, wherein R$^2$ is C$_1$-C$_4$-alkyl.

13. The carboxylate of claim 10, wherein R$^2$ is C$_1$-C$_4$-alkoxy.

14. The carboxylate of claim 10, wherein n is 0.

15. The carboxylate of claim 10, wherein n is 1.

16. The carboxylate of claim 10, wherein R$^3$ is C$_3$-C$_7$-cycloalkyl or C$_3$-C$_7$-cycloalkyl substituted by C$_1$-C$_4$-alkyl, halogen, C$_1$-C$_2$-haloalkyl, C$_3$-C$_4$-alkenyl, C$_2$-C$_4$-haloalkenyl or cyclopentylidenemethyl.

17. The carboxylate of claim 10, wherein R$^3$ is C$_5$-C$_6$-cycloalkenyl or C$_5$-C$_6$-cycloalkenyl substituted by C$_1$-C$_4$-alkyl, halogen, C$_1$-C$_2$-haloalkyl, C$_3$-C$_4$-alkenyl, C$_2$-C$_4$-haloalkenyl or cyclopentylidenemethyl.

18. The carboxylate of claim 10, wherein R$^3$ is hydrogen.

19. The carboxylate of claim 10, wherein R$^3$ is halogen.

20. A process for combating fungi, wherein the fungi or the materials, plants, seed or the soil are treated with a fungicidally effective amount of the carboxylate of claim 10.

21. A fungicide containing an inert carrier and a fungicidally effective amount of the carboxylate of claim 10.

* * * * *